United States Patent
Mann et al.

(10) Patent No.: US 6,749,851 B2
(45) Date of Patent: Jun. 15, 2004

(54) METHODS FOR STERILIZING PREPARATIONS OF DIGESTIVE ENZYMES

(75) Inventors: David M. Mann, Gaithersburg, MD (US); Wilson Burgess, Clifton, VA (US); William N. Drohan, Springfield, VA (US); Yuri Griko, Gaithersburg, MD (US); Martin J. Macphee, Montgomery Village, MD (US)

(73) Assignee: Clearant, Inc., Los Angeles, CA (US)

( * ) Notice: Subject to any disclaimer, the term of this patent is extended or adjusted under 35 U.S.C. 154(b) by 0 days.

(21) Appl. No.: 09/942,938

(22) Filed: Aug. 31, 2001

(65) Prior Publication Data

US 2003/0049245 A1 Mar. 13, 2003

(51) Int. Cl.⁷ .................. A61K 38/46; A61K 38/43; A61L 2/00
(52) U.S. Cl. .................. 424/94.6; 424/94.1; 422/22
(58) Field of Search ................ 424/94.6, 94.1; 422/22; 435/200

(56) References Cited

U.S. PATENT DOCUMENTS

| | | | |
|---|---|---|---|
| RE23,195 E | 2/1950 | Brasch | |
| 2,832,689 A | 4/1958 | Proctor et al. | |
| 2,920,969 A | 1/1960 | Stoddard | |
| 2,962,380 A | 11/1960 | Wertheim | |
| 3,620,944 A | 11/1971 | Tanito | |
| 3,743,480 A | 7/1973 | Falk | |
| 3,779,706 A | 12/1973 | Nablo | |
| 3,962,038 A | 6/1976 | Kawashima et al. | 195/68 |
| 4,136,094 A | 1/1979 | Condie | |
| 4,251,437 A | 2/1981 | Rasmussen et al. | |
| 4,282,863 A | 8/1981 | Beigler et al. | |
| 4,330,626 A | 5/1982 | Blair et al. | |
| 4,336,247 A | 6/1982 | Eriksen | |
| 4,370,264 A | 1/1983 | Kotitschke et al. | |
| 4,409,105 A | 10/1983 | Hayashi et al. | |
| 4,472,840 A | 9/1984 | Jefferies | |
| 4,620,908 A | 11/1986 | Van Duzer | |
| 4,727,027 A | 2/1988 | Wiesehahn et al. | 435/173 |
| 4,784,850 A | 11/1988 | Abraham | |
| 4,798,611 A | 1/1989 | Freeman, Jr. | |

(List continued on next page.)

FOREIGN PATENT DOCUMENTS

| | | |
|---|---|---|
| CA | 2056619 | 10/1991 |
| EP | 310 316 | 4/1989 |
| EP | 334 679 | 9/1989 |
| EP | 919 918 A2 | 6/1999 |
| EP | 919 918 A3 | 6/1999 |
| EP | 0808167 B1 | 6/2002 |
| EP | 0820301 B1 | 7/2002 |
| JP | 408098688 A | 4/1996 |
| JP | 11-216147 | 8/1999 |
| SU | 1321420 A | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 00/28552 | 5/2000 |
| WO | WO 00/52031 | 9/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

P.V. Kapanin et al., "Feasibility of liposome cryoradiation sterilization," Khimiko–Farmatsevicheskii Zhurnal, 1988, vol. 22(4), Abstract, pp. 479–482.

Borisova, E.A. et al., Protein Degradation During Interphase Death of Thymocytes Induced by Radation and Dexamethasone, pp. 519–521 (1990).

Chanderkar, L.P. et al., The Involvement of Aromatic Amino Acids in Biological Activity of Bovine Fibrinogen as Assessed by Gamma–Irradiation, Radiation Research, 65:283–291 (1976) (Academic Press, Inc.).

Chanderkar, L.P. et al., Radiation–Induced Changes In Purified Prothrombin and Thrombin, Biochimica et Biophysica Acta, 706:1–8 (1982) (Elsevier Biomedical Press).

Chin, S. et al., Virucidal Treatment of Blood Protein Products With UVC Radiation, Photochemistry and Photobiology, 65:432–435 (1977) (American Society for Photobiology).

Dyskin, E.A. et al., Hemomicrocirculatory Bed in the Wall of Hollow Organs of the Dog Gastrointestinal Tract at Portal Hypertension, Arkh Anat Gistol Embiol, 93:58–68 (1987).

Ghosh, M.M. et al., A Comparison of Methodologies for the Preparation of Human Epidermal–Dermal Composites, Annals of Plastic Surgery, 39:390–404 (1997) (Lippincott–Raven Publishers).

Goertzen, M.J. et al., Anterior Cruciate Ligament Reconstruction Using Cryopreserved Irradiated Bone–ACL–Bone–Allograft Transplants, Knee Surg. Sports Traumatol. Arthroscopy, 2:150–157 (1994) (Springer–Verlag).

(List continued on next page.)

Primary Examiner—Chris Tate
Assistant Examiner—Randall Winston
(74) Attorney, Agent, or Firm—Fleshner & Kim, LLP

(57) ABSTRACT

Methods are disclosed for sterilizing preparations of digestive enzymes to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. These methods involve sterilizing preparations of digestive enzymes, such as trypsin, α-galactosidase and iduronate-2-sulfatase, with irradiation.

53 Claims, 18 Drawing Sheets

U.S. PATENT DOCUMENTS

| | | | |
|---|---|---|---|
| 4,865,602 A | 9/1989 | Smestad et al. | |
| 4,877,866 A | 10/1989 | Rudnick et al. | 530/387 |
| 4,894,253 A | 1/1990 | Heineman et al. | 427/36 |
| 4,931,361 A | 6/1990 | Baldeschwieler et al. | |
| 4,933,145 A | 6/1990 | Uchida et al. | |
| 4,946,648 A | 8/1990 | Dichtelmüller et al. | |
| 4,963,356 A | 10/1990 | Calenoff et al. | |
| 4,994,237 A | 2/1991 | Login et al. | 422/21 |
| 5,000,951 A | 3/1991 | Bass et al. | |
| 5,002,766 A | 3/1991 | Ransberger et al. | 424/94.2 |
| 5,012,503 A | 4/1991 | Nambu et al. | |
| 5,044,091 A | 9/1991 | Ueda et al. | |
| 5,106,619 A | 4/1992 | Wiesehahn et al. | |
| 5,134,295 A | 7/1992 | Wälischmiller | |
| 5,185,371 A | 2/1993 | Rubinstein | |
| 5,226,065 A | 7/1993 | Held et al. | |
| 5,283,034 A | 2/1994 | Okrongly et al. | |
| 5,362,442 A | 11/1994 | Kent | |
| 5,418,130 A | 5/1995 | Plat. et al. | |
| 5,460,962 A | 10/1995 | Kemp | |
| 5,510,122 A | 4/1996 | Sreebny et al. | |
| 5,548,066 A | 8/1996 | Leneau et al. | |
| 5,603,894 A | 2/1997 | Aikus et al. | |
| 5,609,864 A | 3/1997 | Shanbrom | |
| 5,637,451 A | 6/1997 | Ben-Hur et al. | |
| 5,643,464 A | 7/1997 | Rhee et al. | |
| 5,712,086 A | 1/1998 | Horowitz et al. | |
| 5,730,933 A | 3/1998 | Peterson | |
| 5,817,528 A | 10/1998 | Böhm et al. | |
| 5,837,313 A | 11/1998 | Ding et al. | |
| 5,856,172 A | 1/1999 | Greenwood et al. | |
| 5,881,534 A | 3/1999 | Ahlqvist et al. | |
| 5,911,951 A | 6/1999 | Girardot et al. | 422/28 |
| 5,958,669 A | 9/1999 | Ogle et al. | 435/1.1 |
| 5,965,349 A | 10/1999 | Lin et al. | 435/2 |
| 5,981,163 A | 11/1999 | Horowitz et al. | |
| 5,986,168 A | 11/1999 | Noishiki | |
| 5,989,498 A | 11/1999 | Odland | |
| 6,010,719 A | 1/2000 | Remon et al. | |
| 6,046,024 A | 4/2000 | Burton et al. | |
| 6,049,025 A | 4/2000 | Stone et al. | |
| 6,060,233 A | 5/2000 | Wiggins | |
| 6,066,626 A | 5/2000 | Yew et al. | |
| 6,087,141 A | 7/2000 | Margolis-Nunno et al. | |
| 6,120,592 A | 9/2000 | Brault et al. | |
| 6,159,490 A | 12/2000 | Deghenghi | |
| 6,171,549 B1 * | 1/2001 | Kent | |
| 6,187,572 B1 | 2/2001 | Platz et al. | |
| 6,190,855 B1 | 2/2001 | Herman et al. | |
| 6,197,207 B1 | 3/2001 | Chapman et al. | |
| 6,203,544 B1 | 3/2001 | Gotzen | |
| 6,214,534 B1 | 4/2001 | Horowitz et al. | |
| 6,235,508 B1 | 5/2001 | Sowemimo-Coker et al. | |
| 6,248,547 B1 * | 6/2001 | Laduca | |
| 6,258,821 B1 | 7/2001 | Stogniew et al. | |
| 6,312,931 B1 | 11/2001 | O'Dwyer et al. | 435/173.1 |
| 6,346,216 B1 | 2/2002 | Kent | 422/22 |
| 6,358,284 B1 | 3/2002 | Fearnot et al. | 623/23.72 |
| 6,375,989 B1 | 4/2002 | Badylak et al. | 424/551 |
| 6,383,732 B1 | 5/2002 | Stone | 435/1.1 |
| 6,383,810 B2 | 5/2002 | Fike et al. | 435/384 |
| 6,384,419 B1 | 5/2002 | Purtle | 250/526 |
| 6,461,630 B1 | 10/2002 | Tucker et al. | 424/423 |
| 6,485,723 B1 | 11/2002 | Badylak et al. | 424/93.7 |
| 2001/0049141 A1 | 12/2001 | Fike et al. | 435/384 |
| 2002/0064807 A1 | 5/2002 | Badylak et al. | 435/34 |
| 2002/0106394 A1 | 8/2002 | Tucker et al. | 424/423 |
| 2002/0188319 A1 | 12/2002 | Morris et al. | 606/213 |
| 2003/0068815 A1 | 4/2003 | Stone et al. | 435/325 |

OTHER PUBLICATIONS

Horowitz, B. et al., Inactivation of Viruses in a Labile Blood Derivatives, II. Physical Methods, Transfusion, 25:523–527 (1985).

Hsiue, G. et al., Absorbable Sandwich–Like Membrane for Retinal–Sheet Transplantation, pp. 20–25 (2002) (Wiley Periodicals, Inc).

Jensen, J. et al., Membrane–bound Na, K–ATPase: Target Size and Radiation Inactivation Size of Some of Its Enzymatic Reactions, J. Biological Chemistry, 263:18063–18070 (1988) (Am. Soc. for Biochem. and Mol. Biol.).

Kamat, H.N. et al., Correlation of Structural Alterations in Bovine Fibrinogen with Loss of Clotting Properties After Gamma Radiation, Radiation Research, 49:381–389 (1972) (Academic Press, Inc.).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kuijpers, A.J. et al., In vivo Compatibility and Degradation of Crosslinked Gelatin Gels Incorporated in Knitted Dacron, pp. 137–144 (2000) (John Wiley & Sons, Inc.).

Le Maire, M. et al., Effects of Ionizing Radiation on Proteins, Journal of Biochem., 267:431–439 (1990).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541–546 (1996) (American Society for Photobiology).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Plavsic, Z.M. et al., Resistance of Porcine Circovirus to Gamma Irradation, BioPharm, pp. 32–36 (Apr. 2001).

Potier, M. et al., Radiation Inactivation of Proteins: Temperature–Dependent Inter–Protomeric Energy Transfer in Ox Liver Catalase, Biochem. J., 298:571–574 (1994).

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130–1134 (1978).

Salim–Hanna, M. et al., Free Radical Scavenging Activity Of Carnosine, Free Rad. Res. Comms., 14:263–270 (1991) (Harwood Academic Publishers GmbH).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins, (Jun. 2002) (Abstract).

Suomela, H., Inactivation of Viruses in Blood Plasma Products, Transfusion Medicine Reviews, 7:42–57 (1993) (W.B. Saunders Company).

(Abstract of EP0919198A2 and EP0919198A3 (Delphion–DERABS Abstract #G199–304614)).

Website: www.wslfweb.org/docs/dstp2000.dtopdf/19–MD.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentations, US Army Medical Research and Material Command Combat Casualty Care Research Program (2001).

Website: www.usacc.org/RevisedStepB.html, Bakaltcheva, I. et al. (FY01 Request for Proposals—Intramural—Revised 2, Combat Casualty Care Research Program, (2002)).

Website: www.benvue.com/history/history_content.html, (2002).

Website: www.phase–technologies.com/html/vol.2no1.html, Jennings, T.A., (Glossary of Terms for Lyophilization) (1999).

Website: www.phase–technologies.com/html/vol.1no9.html, Jennings, T.A., Overview of the Lyophilization Process) (1988).

Website: www.phase–technologies.com/html/vol.1no2.html, Jennings, T.A., (What I Wish I Knew About Lyophilization) (1999).

Website: www.phase–technologies.com/html/vol.1no7.html, Jennings, T.A., (Which Shelf Temperature During Lyophilization?) (1988).

Website: www.phase–technologies.com/html/vol.1no10.html, Jennings, T.A., (Yes, You have no Eutectic) (1988).

Robert J. Woods, "Food Irradiation," Endeavor, New Series, vol. 18, No. 3, 1994, pp. 104–108.

A Dziedzic–Goclawska et al., "Sterilisation of Tissue Allografts," Advances in Tissue Banking, vol. 1, pp. 261–321.

M.J. Goertzen et al., "Sterilisation of Canine Anterior Cruciate Allografts by Gamma Irradiation in Argon," Journal of Bone and Joint Surgery (Corrections), vol. 77–B, No. 2, Mar. 1995, pp. 205–212.

AABB FDA Liaison Meeting, ABC Newsletter, Dec. 12, 1997, p. 14.

Ozan Akkus et al., Fracture Resistance of Gamma Radiation Sterilized Cortical Bone Allografts, 2001, pp. 927–934, Journal of Orthopaedic Research, vol. 19.

Tikvah Alper et al., The Exceptionally Small Size of the Scrapie Agent, 1966, pp. 278–284, Biochemical and Biophysical Research Communications, vol. 22, No. 3.

Tikvah Alper et al., Protection by Anoxia of the Scrapie Agent and Some DNA RNA Viruses Irradiated as Dry Preparations, 1968, pp. 157–166, J. Gen Virol., vol. 3.

Tikvah Alper et al., Does the Agent of Scrapie Replicate Without Nucleic Acid? May 20, 1967, pp. 764–766, Nature, vol. 214.

Tikvah Alper et al., The Scrapie Agent: Evidence Against its Dependence For Replication on Intrinsic Nucleic Acid, 1978, pp. 503–516, J. Gen. Virol., vol. 41.

S.R. Aparicio et al., Light and Electron Microscopy Studies on Homograft and Heterograft Heart Valves, 1975, pp. 174–162, J. Path, vol. 115.

J. Baksa et al., The Use of Pig's Skin (xenograft) for the Treatment of Burns, 1976, pp. 138–145, Magyar Traumatologin, vol. 19.

Michael L. Baldwin et al., Irradiation of Blood Components, 1992, pp. 10–78, American Association of Blood Banks.

R.H. Bassin et al., Abrogation of Fv-1$^b$Restriction With Murine Leukemia Viruses Inactivated by Heat or by Gamma Irradiation, May 1978, pp. 306–315, Journal of Virology, vol. 26, No. 2.

Guy Beauregard et al., Temperature Dependence of the Radiation Inactivation of Proteins, 1985, pp. 117–120, Analytical Biochemistry, vol. 150.

Sandra Blakeslee, Tight Rules on Use of Organs Do Not Apply to Tissues, Jan. 20, 2002, The New York Times Newspaper.

Seymour S. Block, Disinfection, Sterilization, and Preservation, Fundamental Principles of Activity Principles of Antimicrobial Activity, Fourth Edition, 1991, pp. 31–33.

A.J.J.C. Bogers et al., Long–Term Results of the Gamma–Irradiation–Preserved Homograft Monocusp for Transannular Reconstruction of the Right–Ventricular Outflow Tract in Tetralogy of Fallot, 1994, pp. 337–330, Thorac. Cardiovasc. Surgeon, vol. 42.

David R. Brown et al., Antioxidant Activity Related to Copper Binding of Native Prion Protein, 2001 pp. 69–76, Journal of Neurochemistry, vol. 76.

P. Brown, The Risk of Blood–Borne Creutzfeldt–Jakob Disease, 1999, pp. 53–59, Advances in Transfusion Safety Dev. Biol. vol. 102.

P. Brown et al., Further Studies of Blood Infectivity in an Experimental Model of Transmissible Spongiform Encephalopathy, With an Explanation of Why Blood Components Do Not Transmit Jacob–Creutzfeldt–Jakob Disease in Humans, Nov./Dec. 1999, pp. 1169–1178, Transfusion, vol. 39.

Paul Brown et al., Effect of Chemicals, Heat, and Histopathologic Processing on High–Infectivity Hamster–Adapted Scrapie Virus, May 1982, pp. 683–687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pp. 810–816, Transfusion, vol. 38.

D.G. Campbell et al., Sterilization of HIV With Irradiation: Relevance to Infected Bone Allografts, 1999, pp. 517–521, Aust. N.Z.J. Surg., vol. 69.

Ernest U. Conrad et al., Transmission of the Hepatitis–C Virus by Tissue Transplantation, Feb. 1995, pp. 214–224, The Journal of Bone and Joint Surgery, vol. 77–A, No. 2.

A.S. Dagli, Correction of Saddle Nose Deformities by Coral Implantation, 1997, pp. 274–276, Eur. Arch. Otorhinolaryngol, vol. 254.

Defeng et al., Sterilization of Silver–Acidum Pipemedicum Skin for the Treatment of Burns by Radioactive Cobalt–60–.Gamma.–Ray, 1995, pp. 406 (Abstract).

P. Di Simplico et al., The Reactivity of the SH Group of Bovine Serum Albumin With Free Radicals, 1991, pp. 253–262, Free Rad. Comms., vol. 14, No. 4.

R.J. Donnelly et al., Gamma–radiation of Heart Valves at 4° C; A Comparative Study Using Techniques of Histochemistry and Electron and Light Microscopy, 1973, pp. 95–101, Thorax, vol. 28.

Duane C. Eichler et al., Radiation Inactivation Analysis of Enzymes, Jul. 15, 1987, pp. 9433–9436, The Journal of Biological Chemistry, vol. 262, No. 20.

Luanne H. Elliott et al., Inactivation of Lassa, Marburg and Ebola Viruses by Gamma Irradiation, Oct. 1982, pp. 704–708, Journal of Clinical Microbiology, vol. 16, No. 4.

Bradley M. Fideler et al., Gamma Irradiation: Effects on Biomechanical Properties of Human Bone–Patellar Tendon–Bone Allografts, 1995, pp. 643–646, American Journal of Sports Medicine, vol. 23, No. 5.

Bradley M. Fideler et al., Effects of Gamma Irradiation on the Human Immunodeficiency Virus, Jul. 1994, The Journal of Bone and Joint Surgery, vol. 76–A, No. 7.

Fields et al., Susceptibility of Scrapie Agent to Ionizing Radiation, Apr. 5, 1969, pp. 90–91, Nature, vol. 222.

M.J. Gibbons et al., Effects of Gamma Irradiation on the Initial Mechanical and Material Properties of Goat Bone Patellar Tendon–Bone Allografts, 1991, pp. 209–218, J. Orthop Res, vol. 9, No. 2.

J.R.P. Gibbons et al., Gamma Ray Sterilisation of Homograft Valves, 1969, pp. 353–358, Bulletin De La Societe Internationale De Chirugie, No. 3.

M.J. Goertzen et al., Anterior Cruciate Ligament Reconstruction Using Cryopreserved Irradiated Bone–ACL–Bone Allograft Transplants, 1994, pp. 150–157, Knee Surgery Sports Traumatology Arthroscopy, vol. 2.

M.J. Goertzen et al., Sterilisation of Canine Anterior Cruciate Allografts by Gamma Irradiation in Argon, Mar. 1995, pp. 205–212, The Journal of Bone and Joint Surgery, vol. 77–B, No. 2.

Slawomir Gregorczyn et al., Strength and Lyophilized and Irradiated Cortical Bone of the Human Femur, 1995, pp. 129–133, Chir. Narz. Ruchu Ortop. Pol., Lx 2.

D.A. Haig, Further Studies on the Inactivation of the Scrapie Agent by Ultraviolet Light, 1969, pp. 445–457, J. Gen. Virol., vol. 5.

F.W. Hehrlein et al., Biochemische Veränderungen an Heterologen Aortenklappentransplantaten nach Anwendung Verschiedener Sterilisationsverfahren, pp. 1183–1185, Langenbecks Arch. Chir., Bd. 325 (Kongrebericht) (English Summary found at p. 1183).

F.W. Hehrlein et al., Morphologische Utersuchungen an Heterologen Herzklappentransplantaten Unter Verschiedenen Sterilisationbedingungen, pp. 244–251(English Summary found at p. 250).

H. Hiemstra et al., Inactivation of Human Immunodeficiency Virus by Gamma Radiation and its Effect on Plasma and Coagulation Factors, 1991, pp. 32–39, Transfusion, vol. 31, No. 1.

Richard Hinton et al., A Biochemical Analysis of Solvent–dehydrated and Freeze–Dried Human Fascia Lata Allografts, 1992, pp. 607–612, The American Journal of Sports Medicine, vol. 20, No. 5.

B. Horowitz et al., Inactivation of Viruses in Labile Blood Derivatives, II. Physical Methods, 1985, pp. 523–527, Transfusion, vol. 25, No. 6.

M. Horowitz, Sterilization of Homograft Ossicles by Gamma Radiation, Nov. 1979, pp. 1087–1089, The Journal of Laryngology and Otology, vol. 93.

Carol House et al., Inactivation of Viral Agents in Bovine Serum by Gamma Irradiation, 1990 pp. 737–740, Can. J. Microbiol., vol. 36.

Shinichiro Ijiri et al., Effect of Sterilization on Bone Morphogenetic Protein, 1994, pp. 628–636, Journal of Orthopedic Research, vol. 12.

A.S. Imamaliev et al., Biological Properties of Bone Tisue Conserved in Plastic Material and Sterilized With Gamma Rays, 1974, pp. 129–135, ACTA, Chirugiae Plasticae, vol. 16, No. 3.

A. Ingegneri et al., An 11–Year Assessment of 93 Flash–frozen Homograft Valves in the Aortic Position, 1979, pp. 304–307, Thorac. Cardiovasc. Surgeon, vol. 27.

J. Jerosch et al., A New Technique for Bone Sterilization, 1989, pp. 117–120, Biomedizinische Technik, Band 34, Heft 5.

J. Jerosch et al., Influence of Different Rehydration Periods on the Stability and the Water Content of Bone Allografts After Lyophilization, Gamma–Irradiation, and Lipid Extraction, 1994, pp. 335–341, Z. Orthop., vol. 132.

J.D. Keathley et al., Is There Life After Irradiation? Part 2: Gamma–Irradiated FBS in Cell Culture Jul./Aug. 1993, pp. 46–52, BioPharm.

E.S. Kempner et al., Size Determination of Enzymes by Radiation Inactivation, 1979, pp. 2–10, Analytical Biochemistry, vol. 92.

L. Kerboull et al., In Vitro Study of the Influence of Avrious Conservation Methods on the Mechanical Properties of Patellar Tendon Allografts, 1991, pp. 751–762, Chirurgie, vol. 117.

A.D. Kitchen, Effect of Gamma Irradiation on the Human Immunodeficiency Virus and Human Coagulation Proteins, 1989, pp. 223–229, Vox Sang, vol. 56.

Andrezej Komender et al., Some Biological Properties of Bovine Trypsinized Facia Xenografts, 1981, pp. 485–489, Archivum Immunologiae et Therapie Experimentalis, vol. 29.

Andrezej Komendar et al., Some Biological Properties of Preserved Bovine Fascia Enrighed With Pulverized Calf Cartilage, 1984, pp. 211–219, Archivum Immunologie et Therapiae Experimentalis, vol. 32.

J.F. Kouvalchouk et al., The Use of Sterilized Bone Allografts in Reconstruction After Tumour Resection, 1986, pp. 393–401, Revue de Chirurgie Orthopedique, vol. 72.

Raymond Latarjet, Inactivation of the Agents of Scrapie, Cruetzfeldt–Jakob Disease, and Kuru by Radiations; 1979, pp. 387–407, Slow Transmissible Diseases of the Nervous System, vol. 2.

R. Latarjet et al., Inactivation of the Scrapie Agent by Near Monochromatic Ultraviolet Light, Sep. 26, 1970, pp. 1341–1343, Nature. vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pp. 449–455, Transfusion, vol. 41.

Susan F. Leitman, Use of Blood Cell Irradiation in the Prevention of Posttransfusion Graft–vs–Host Disease, 1989, pp. 219–232, Transf. Sci., vol. 10.

Linberg et al., Irradiated Homologous Cartilage For Orbital Reconstruction, Jul. 1980, pp. 457–462, Ophthalmic Surgery, vol. 11.

Sandra McDowell, Irradiated Cartilage, Spring 1988, pp. 14–15, Plastic Surgical Nursing.

A. Maeda et al., Effects of Solvent Preservation With or Without Gamma Irradiation on the Material Properties of Canine Tendon Allografts, 1993, pp. 181–189, Journal of Orthopaedic Research, vol. 11.

Akira Maeda et al., Solvent–dried and Gamma–irradiated Tendon Allografts in Rats, Jul. 1998, pp. 731–736, The Journal of Bone and Joint Surgery, vol. 80–B, No. 4.

S. Malawski et al., The Use of Dry–Freezed Bone Grafts Sterilized by Gamma Rays in Orthopaedic Surgery, 1969, pp. 61–68, Chir. Narz. Ruchu Ortop.

Linda Marton et al., Disinfection and Inactivation of the Human T. Lymphotrogic Virus Type III/Lymphadenopathy–Associated Virus, Aug. 1985, pp. 499–403, The Journal of Infectious Diseases, vol. 151, No. 2.

S.I. Miekka et al., New Methods for Inactivation of Lipid–enveloped and Non–enveloped Viruses, 1998, pp. 402–408, Haemophilia, vol. 4.

Ken Nakata et al., Reconstruction of the Lateral Ligaments of the Ankle Using Solvent–dried and Gamma–Irradiated Allogeneic Fascia Lata, May 2000, pp. 579–582.

Maria Esther Martinez Pardo et al., Clinical Application of Amniotic Membranes on a Patient With Epidermoloysis Bullosa, 1999, pp. 68–73, Annals of Transplantation, vol. 4, No. 3–4.

Jan Parizek et al., Duraplasty With Pretreated Freeze–Dried Sterilized Human Dura Mater, 1990, pp. 135–143, Sbor. ved. Praci LF UK Hradee Kralove, vol. 33.

Jan Parizek et al., Ovine Pericardium: A New Material For Duraplasty, 1996, pp. 508–513, J. Neurosurg., vol. 84.

Patel et al., Effect of Gamma Radiation and Ethylene Oxide on Papain, 1979, pp. 81–83, Indian J. Pharm. Sci., vol. 41, No. 2.

L.V. Polezhaeu et al., Repair of Cranial Defects With Regenerating Bone in Grafting Gamma–Irradiated Bone Filings, pp. 57–60.

Pollard, The Effect of Ionizing Radiation on Viruses, pp. 65–71.

Donald J. Prolo et al., Composite Autogenic Human Cranioplasty: Frozen Skull Supplemental With Fresh Iliac Corticocancellous Bone, Dec. 1984, pp. 846–851, Neurosurgery, vol. 15, No. 6.

Donald J. Prolo et al., Superior Osteogenesis in Transplanted Allogeneic Canine Skull Following Chemical Sterilization, Aug. 1982, pp. 230–242, Clinical Orthopaedics and Related Research, No. 168.

Elena Quaglio et al., Copper Converts the Cellular Prion Protein Into a Protease–resistant Species That Is Distinct From the Scrapie Isoform, Apr. 6, 2001, pp. 11432–11438, The Journal of Biological Chemistry, vol. 276, No. 14.

T.J. Rasmussen et al., The Effects of 4 Mrad of Gamma–Irradiation on the Initial Mechanical Properties of Bone–Patellar Tendon–Bone Grafts, 1994, pp. 188–197, The Journal of Arthroscoic and Related Surgery, vol. 10, No. 2.

Brian D. Reid, The Sterways Process: A New Approach to Inactivating Viruses Using Gamma Radiation, 1998, pp. 125–130, Biologicals, vol. 26.

S.C. Roe et al., The Effect of Gamma Irradiation on a Xenograft Tendon Bioprothesis, 1992, pp. 149–154, Clinical Materials, vol. 9.

Robert G. Rohwer, Estimation of Scrapie Nucleic Acid MW From Standard Curves for Virus Sensitivity to Ionizing Radiation, Mar. 27, 1986, pp. 381; Nature, vol. 320, No. 6060.

Robert G. Rohwer, Scrapie Infectious Agent is Virus–like in Size and Susceptibility to Inactivation, Apr. 12, 1984, pp. 658–662, Nature, vol. 308.

R.G. Rohwer, The Scrapie Agent: A Virus by Any Other Name, pp. 195–232, Current Topics in Microbiology and Immunology, vol. 172.

Robert W. Rohwer et al., Scrapie–Virus or Viroid, The Case For a Virus, pp. 333–335, Laboratory of Central Nervous System Studies, National Institutes of Neurological and Communicative Disorders and Stroke, National Institute of Health.

Robert G. Rohwer, Virus–Like Sensitivity of the Scrapie Agent to Heat Inactivation, Feb. 10, 1984, pp. 600–602, Science, vol. 223.

Robert Sullivan et al., Inactivation of Thirty Viruses by Gamma Radiation, Jul. 1971, pp. 61–65, Applied Microbiology, vol. 22, No. 1.

D. Tylman, Mechanical Character of Liofilized and Sterilized by Gamma–Rays Bone Tissue, 1996, pp 229–234, Chirurgia Narzadow Ruchi I, Ortopedia Polska.

W. Welch, A Comparative Study of Different Methods of Processing Aortic Homografts, 1969, pp. 746–749, Thorax, vol. 24.

J.M. White et al., Sterilization of Teeth by Gamma Radiation, Sep. 1994, pp. 1560–1567, J. Dent. Res., vol. 73, No. 9.

Boon–Seng Wong et al., Copper Refolding of Prior Protein, 2000, pp. 1217–1224, Biochemical and Biophysical Research Communications, vol. 276.

Boon–Seng Wong et al., Differential Contribution of Superoxide Dismutase Activity by Prior Protein in Vivo, 2000, pp. 136–139, Biochemical and Biophysical Research Communications, vol. 273.

Boon–Seng Wong et al., Prion Disease: A Loss of Antioxidant Function? 2000, pp. 249–252, Biochemical and Biophysical Research Communications, vol. 275.

D.E. Wyatt et al., Is There Life After Irradiation? Part I: Inactivation of Biological Contaminants, Jun. 1993, pp. 34–39, BioPharm.

Qi Zhang et al., Ethylene Oxide Does Not Extinguish the Osteoinductive Capacity of Demineralized Bone, 1997, pp. 104–108, Acta Orthop. Scand, vol. 68, No. 2.

Yongxing Zhang et al., A Comprehensive Study of Physical Parameters, Biochemical Properties and Statistical Correlations of Iliac Crest Bone Wedges Used in Spinal Fusion Surgery, 1994, pp. 304–308, Spine, vol. 19, No. 3.

License Amendment and procedures for Gamma Irradiation of Blood Products, Jun. 22, 1993, pp. 1–18, Dept. of Health & Human Services, Food and Drug Administration.

M.F. Alladine et al., γ–Radiation Damage to Starr–Edwards Valves, Mar. 16, 1998, pp. 68, The Lancet, Letters to the Editor.

Ch. Baquey et al., Radiosterilization of Albuminated Polyester Prostheses, May 1987, pp. 185–189, Biomaterials, vol. 8.

Edward H. Bedrossian, Jr., HIV and Banked Fascia Lata, 1991, pp. 284–288, Opthalmic Plastic and Reconstructive Surgery, vol. 7, No. 4.

Liu Bingci, Mouse Antibody Response Following Repetitive Injections of Gamma–Irradiated Human Placenta Collagen, Jun. 1994, pp. 100–103, Chinese Medical Sciences Journal, vol. 9, No. 2.

A.A. Belov et al., The Influence of γ–Radiation on Enzyme Activity of Collalitin in the in the Process of Storage, Dec. 7, 1989, pp. 519–521, All–Union Research Institute of Textile and Haberdashery Industry, Moscow.

R.G. Burwell, The Fate of Freeze–Dried Bone Allografts, Jun. 1976, pp. 95–111, Transplantation Proceedings, vol. VII, No. 2, Supplement 1.

L. Callegaro et al., Hollow Fiber Immobilized L–Asparginase: In Vivo and In Vitro Immunological Studies, 1983, pp. 91–96, The International Journal of Artificial Organs, vol. 6, No. 2.

G. Campalani et al., Aortic Valve Replacement With Frozen Irradiated Homografts, 1989, pp. 558–561, Eur. J. Cardio–thoracic Surgery, vol. 3.

David T. Cheung et al., The Effect of γ–Irradiation on Collagen Molecules, Isolated α–chains, and Crosslinked Native Fibers, 1990, pp. 581–589, Journal of Biomedical Materials Research, vol. 24.

David J. Cohen et al., The Fate of Aortic Valve Homografts 12 to 17 Years After Implantation, Mar. 1988, pp. 482–484, Chest, vol. 93, No. 3.

A.G. Churchalin et al., Clinical Immunosorbents Basing On Space–Network Polymers, 1998, pp. 1524–1529, All Union Research Institute of Chemical Reagents and Chemicals of Special Purity, Moscow.

P. De Deyne et al., Some Effects of Gamma Irradiation on Patellar Tendon Allografts, 1991, pp. 51–62, Connective Tissue Research, vol. 27.

R.I. Vaida et al., Structural–Functional Peculiarities of Myocardial Capillaries After Resection of the Lungs, Oct. 21, 1986, pp. 68–73.

R. Guidoin et al., A Compound Arterial Prosthesis: The Importance of the Sterilization Procedure on the Healing and Stability of Albuminated Polyester Grafts, Mar. 1985, pp. 122–128, Biomaterials, vol. 6.

Ph. Hernigou et al., Radiation Sterilization of Bone and the HIV Virus, 1993, pp. 445–451, Revue de Chirurgie Orthopedique, vol. 79.

Hsing–Wen Sung et al., Effects of Various Chemical Sterilization Methods on the Crosslinking and Enzymatic Degradation Characteristics of an Epoxy–Fixed Biological Tissue, Dec. 1996, pp. 376–383, Sterilization of Biological Tissues.

James R. Malm et al., An Evaluation of Aortic Valve Homografts Sterilized by Electron Beam Energy, Oct. 1967, pp. 471–477, Journal of Thoracic and Cardiovascular Surgery, vol. 54, No. 4.

James R. Malm et al., Results of Aortic Valve Replacement Utilizing Irradiated Valve Homografts, pp. 740–747, Annals New York Academy of Sciences.

W. Oh et al., Mitral Valve Replacement With Preserved Cadaveric Aortic Homografts, May 1973, pp. 712–721, The Journal of Thoracic and Cardiovascular Surgery, vol. 65, No. 5.

K. Pietrucha, New Collagen Implant As Dural Substitute, Apr. 1991, pp. 320–323, Biomaterials, vol. 12.

Maria Raptopoulou–Gigi et al., Antimicrobial Proteins in Sterilised Human Milk, Jan. 1, 1977, pp. 12–14, British Medical Journal, vol. 1.

Edward A. Rittenhouse et al., Sterlization of Aortic Valve Grafts for Transplantation, Jul. 1970, pp. 1–5, Aortic Valve Grafts for Transplantation, Archives of Surgery, vol. 101, No. 1.

H. Sato et al., Sterilization of Therapeutic Immunoadsorbents by Ionizing Radiation, 1986, pp. 131–136, The International Journal of Artificial Organs, vol. 9, No. 2.

Richard A. Smith et al., Gamma Irradiation of HIV–1, 2001, pp. 815–819, Journal of Orthopaedic Research, vol. 19.

Barbara Lüssi–Schlatter et al., Die Antimikrobielle Behandlung von Peroralen Enzympräparaten mit Gamma–Strahlen, Pharmazeutisches Institut der Eidgenössichen Technischen Hochschule Zürich Galenische Abteilung.

Martindale's Extra Pharmacopoecia, Glucose p. 1265; prior art.

The Merck Index, Eleventh Edition Glucose pp. 4353–4354, prior art.

G.L. Moore et al., Effects of 4000 Rad. Irradiation on the In Vitro Storage Properties of packed Red Cells, Nov.–Dec. 1985, pp. 583–585, Final Rept., Pub. In Transfusion, vol. 25, No. 6 (Abstract).

Shcheglova et al., The Effect of the Power of Gamma–Radiation on the Radiation Dose in the Sterilization of Drugs, 1984, pp. 730–732, Khim–Farm Zh, vol. 18, No. 6 (Abstract).

G.A. Yarygina, Dose Rate Effect on Survival of Microorganisms Used as Test–Cultures in Radiation Sterilization of Medical Products, 1973, pp. 32–39, Radiats. Tekh., No. 9 (Abstract).

O. Cornu et al., Effect of Freeze–Drying and Gamma Irradiation on the Mechanical Properties of Human Cancellous Bone, 2000, pp. 426–431, Journal of Orthopaedic Research, vol. 18.

Anna Dziedzic–Goclawska et al., Effect of Radiation Sterlization on the Osteoinductive Properties and the Rate of Remodeling of Bone Implants Preserved by Lyophilization and Deep–Freezing, Nov. 1991, pp. 30–37, Clinical Orthopaedics and Related Research, vol. 272.

Ole T. Jensen et al., Vertical Guided Bone–Graft Augmentation in a New Canine Mandibular Model, Nov. 3, 1995, pp. 335–343, The International Journal of Oral and Maxillofacial Implants, vol. 10.

Ronald W. Katz et al., Radiation–Sterilized Insoluble Collagenous Bone Matrix is a Functional Carrier of Osteogenin for Bone Induction, 1990, pp. 183–185, Calcified Tissue International, vol. 47.

Everard Munting et al., Effect of Sterilization on Osteoinduction, 1988, pp. 34–38, Acta Orthop Scand, vol. 59, No. 1.

P.A. Puolakkainen et al., The effect of Sterilization on Transforming Growth Factor $\beta$ Isolated From Demineralized Human Bone, 1993, pp. 679–685, Transfusion, vol. 33, No. 8.

U. Ripamonti et al., Long–Term Evaluation of Bone Formation by Osteogenic Protein 1 in the Baboon and Relative Efficacy of Bone–Derived Bone Morphogenetic Proteins Delivered by irradiated Xenogeneic Collageneous Matrices, 2000, pp. 1798–1809, Journal of Bone and Mineral Research, vol. 15, No. 9.

A. Salehpour et al., Dose–Dependent Response of Gamma Irradiation on Mechanical Properties and Related Biochemical Composition of Goat Bone–Patellar Tendon–Bone Allografts, 1995, pp. 898–906, The Journal of Orthopaedic Research, vol. 13.

Nikolaus Schwarz et al., Irradiation–sterilization of Rat Bone Matrix Gelatin, 1988, pp. 165–167, Acta Orthop Scand, vol. 59, No. 2.

C.W. Smith et al., Mechanical Properties of Tendons: Changes With Sterilization and Preservation, Feb. 1996, pp. 56–61, Journal of Biomechanical Engineering, vol. 118.

Yukiyoshi Toritsuka et al., Effect of Freeze–Drying or γ–Irradiation on Remodeling of Tendon Allograft in a Rat Model, 1997, pp. 294–300, Journal of Orthopaedic Research, vol. 15.

Konrad Wangerin et al., Behavior of Differently Sterilized Allogenic Lyophilized Cartilage Implants in Dogs, 1987, pp. 236–242, J. Oral Maxillofac Surg, vol. 45.

S. Wientroub et al., Influence of Irradiation on the Osteoinductive Potential of Demineralized Bone Matrix, 1988, pp. 255–260, Calcified Tissue International, vol. 42.

\* cited by examiner

METHODS FOR STERILIZING PREPARATIONS OF DIGESTIVE ENZYMES

FIELD OF THE INVENTION

The present invention relates to methods for sterilizing preparations of digestive enzymes to reduce the level of one or more active biological contaminants or pathogens therein, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. The present invention particularly relates to methods of sterilizing preparations of digestive enzymes, such as trypsin, α-galactosidase and iduronate 2-sulfatase, with irradiation.

BACKGROUND OF THE INVENTION

The principal foods upon which an organism, such as a human, survives can be broadly categorized as carbohydrates, fats and proteins. These substances, however, are useless as nutrients without the process of digestion to break down foods.

Digestion of carbohydrates begins in the mouth and stomach. Saliva contains the enzyme ptyalin (an alpha-amylase), which hydrolyses starch into maltose and other small polymers of glucose. The pancreatic alpha-amylase is similar to the salivary ptyalin, but several times as powerful. Therefore, soon after chyme empties into the duodenum and mixes with pancreatic juice, virtually all of the starches are converted into disaccharides and small glucose polymers. These disaccharides and small glucose polymers are hydrolysed into monosaccharides by intestinal epithelial enzymes.

Digestion of proteins begins in the stomach. The enzyme pepsin, which is produced in the stomach, digests collagen, a major constituent of the intercellular connective tissue of meats. This enzymatic reaction is essential so that other digestive enzymes can penetrate meats and digest the cellular proteins. Consequently, in people who lack peptic activity in the stomach, the ingested meats are not well penetrated by these other digestive enzymes and so are poorly absorbed.

Most protein digestion results from the actions of the pancreatic proteolytic enzymes. Proteins leaving the stomach in the form of proteoses, peptones and large polypeptides are digested into dipeptides, tripeptides and the like by pancreatic proteolytic enzymes or polypeptidases. Trypsin and chymotrypsin split protein molecules into smaller polypeptides at specific peptide linkages, while carboxypolypeptidase cleaves amino acids from the carboxyl ends of polypeptides. Proelastase gives rise to elastase, which in turn digests the elastin fibers that hold together most meat.

Further digestion of polypeptides takes place in the intestinal lumen. Aminopolypeptidase and several polypeptidases split large polypeptides into dipeptides, tripeptides and amino acids, which are transported into the enterocytes that line the intestinal villi. Inside the enterocytes, other polypeptidases split the remaining peptides into their constituent amino acids, which then enter the blood.

Digestion of fats first requires emulsification by bile acids and lecithin, which increase the surface area of the fats up to 1000-fold. Because lipases are water-soluble digestive enzymes that can bind only on the surface of a fat globule, this emulsification process is important for the complete digestion of fat. The most important digestive enzyme in the digestion of triglycerides is pancreatic lipase, which breaks these down into free fatty acids and 2-monoglycerides. After these free fatty acids and monoglycerides enter the enterocytes, they are generally recombined into new triglycerides. A few monoglycerides, however, are further digested by intracellular lipases into free fatty acids.

Digestion therefore continues after the breakdown and uptake of nutrients into the various cells of the body. Intracellular enzymes, such as intracellular lipases, are involved in the uptake, breakdown, transport, storage, release, metabolism and catabolism of nutrients into forms required and useable by the cell(s) of an organism at various places and times. This includes storage of lipids and their metabolism into energy sources as well as their catabolism and synthesis into other useful compounds. Digestion may also occur as a part of an organism's normal process(es) of tissue generation and regeneration or repair of degraded, damaged or abnormal tissue(s) or molecules. It may also be a feature of or result from apoptosis, immune reactions, infections, neoplasms and other abnormal or disease states of an organism.

Preparations of digestive enzymes are therefore often provided therapeutically to humans and animals.

For example, in cases of pancreatitis and lack of pancreatic secretion, preparations of certain pancreatic enzymes, including combinations of lipase, protease and amylase (such as Creon™, Cotazym™, Donnazyme™, Ku-Zyme™ HP, Pancrease™ and Pancrease™ MT, Ultrase™ and Ultrase™ MT, Viokase™, and Zymase™) and combinations of lipase, protease, amylase and cellulase (such as Ku-Zyme™ and Kutrase™), are administered to ensure proper patient nutrition. The digestive enzymes of particular interest, for example in replacement therapy in humans and animals, therefore include pancreatic digestive enzymes, such as trypsin and chymotrypsin, and functional mutants, variants and derivatives thereof.

Trypsin is an enzyme that acts to degrade protein; it is often referred to as a digestive enzyme, or proteinase. In the digestive process, trypsin acts with the other proteinases to break down dietary protein molecules to their component peptides and amino acids. Trypsin continues the process of digestion (begun in the stomach) in the small intestine where a slightly alkaline environment (about pH 8) promotes its maximal enzymatic activity. Trypsin, produced in an inactive form by the pancreas, is remarkably similar in chemical composition and in structure to the other chief pancreatic proteinase, chymotrypsin. Both enzymes also appear to have similar mechanisms of action; residues of histidine and serine are found in the active sites of both. The chief difference between the two molecules seems to be in their specificity, that is, each is active only against the peptide bonds in protein molecules that have carboxyl groups donated by certain amino acids. For trypsin these amino acids are arginine and lysine, for chymotrypsin they are tyrosine, phenylalanine, tryptophan, methionine, and leucine. Trypsin is the most discriminating of all the digestive enzymes in terms of the restricted number of chemical bonds that it will attack.

Preparations of other digestive enzymes, such as glycosidases, are likewise administered therapeutically to human patients. For example, Fabry disease is an X-linked recessive glycolipid storage disorder caused by a deficiency of the lysosomal enzyme α-galactosidase A. Clinical manifestations of Fabry disease included recurrent episodes severe pain and progressive renal, cardiac and cerebrovascular deterioration with death usually occurring in the fourth to sixth decade of life. Enzyme replacement therapy by infusion of a preparation of α-galactosidase A has been tested and found to be a promising potential therapy for this condition (Schiffmann, et al, "Enzyme Replacement Therapy in Fabry Disease: A Randomized Controlled Trial." *JAMA*, Jun. 6, 2001, Vol. 285, No. 21, pp. 2743–2749.).

Glycogen Storage Disease Type II (also known as Acid Maltase Deficiency or Pompe Disease) is another genetically transmitted storage disorder. In GSD-II, the patient suffers from a deficiency of acid maltase enzyme, which breaks down glycogen in muscle cells. Clinical manifestations of GSD-II include progressive muscle weakness due to a build up of glycogen in muscle tissues, eventually resulting in respiratory and/or cardiac failure. Preparations of glycosidases, or functional mutants or variants or derivatives thereof, are therefore also of particular interest for therapeutic use.

Niemann-Pick Disease is also a genetically transmitted metabolic disorder in which harmful quantities of a fatty substance, sphingomyelin, accumulate in the spleen, liver, lungs, bone marrow and brain. Patients suffer from a deficiency of sphingomyelinases, which initiates the biodegradation of sphinogmyelin. Clinical manifestations include enlargement of the spleen and liver, and frequently results in death, particularly for pediatric patients.

Gaucher's Disease is a somewhat-similar genetically transmitted disorder, in which harmful quantities of another fatty substance, glucocerebroside, accumulate in the spleen, liver, lungs, bone marrow and brain. Patients suffer from a deficiency in β-glucocerebrosidase, which catalyzes the first step in the biodegradation of glucocerebroside, which arises from the biodegradation of old red and white blood cells. Clinical manifestations include enlargement of the spleen and liver, low blood platelets, fatigue and, in certain forms, progressive brain damage. Enzyme replacement therapy by infusion of a preparation of a modified form of glucocerebrosidase, known as algucerase (Ceredase™) has been tested and found to be a promising potential therapy for this condition (Barton, et al., "Replacement Therapy for Enzyme Deficiency: Macrophage-targeted Glucocerebrosidase for Gaucher's Disease." *New Engl. J. Med.*, May 23, 1991.).

Mucopolysaccharidoses are a group of inherited metabolic disorders caused by a deficiency in the lysosomal enzymes needed to break down mucopolysaccharides, long chains of sugar molecules used to build connective tissue and organs in the body. A deficiency in one or more of these enzymes cases a build up of excess amount in the body, causing progressive damage and eventual death. Among these disorders are Hurler, Scheie and Hurler/Scheie syndromes (the most severe form, occurs in infancy with death resulting before age 10 years, symptoms include clouding of the cornea and progressive physical and mental disability, caused by a deficiency in α-L-iduronidase), Hunter syndrome (affects juveniles with death usually resulting by age 15 years, symptoms include joint stiffness, mental deterioration, dwarfing and progressive deafness, caused by a deficiency in iduronate-2-sulfatase), Sanfillipo syndrome (death usually occurs by late teens, symptoms include progressive dementia and mental deterioration in childhood, caused by a deficiency in heparan N-sulfatase, α-N-acetylglucosaminadase, acetyl-CoA-glucosaminide acetyltransferase and/or N-acetylglucosamine-6-sulfatase), Morquio syndrome (appears in infancy, symptoms include severe dwarfing and corneal clouding, cardiac or respiratory disease may cause death in third or fourth decade of like, caused by a deficiency in galactosamine-6-sulfatase and/or β-galactosidase), Maroteauz-Lamy syndrome (resembles Hurler syndrome, onset in infancy, but no mental disability, death usually occurs in second or third decade of life, caused by a deficiency in arylsulfatase B), and Sly disease (symptoms include corneal clouding, skeletal irregularities, and enlargement of the liver and spleen, caused by a deficiency in β-glucuronidase). Hunter syndrome is particularly linked to a deficiency in iduronate-2-sulfatase, which catalyzes the breakdown of heparan sulfate and dermatan sulfate, and it has been suggested that this condition can be treated by administration of variant forms of the enzyme (U.S. Pat. No. 6,153,188). The digestive of particular interest, for example in therapy in humans and animals, therefore also include iduronate-2-sulfatase and functional mutants, variants and derivatives thereof.

Multiple Sulfatase Deficiency (also known as Disorder of Confication 13 or Mucosulfatidosis) is another hereditary metabolic disorder characterized by impairment of all known sulfatase enzymes (including arylsulfatases A, B and C, two steroid sulfatases and four other sulfatases). Clinical manifestations include coarse facial features, deafness, an enlarged liver and spleen, abnormalities of the skeleton (including lumbar kyphosis) and dry, scaly skin (ichthyosis).

Similarly, preparations of digestive enzymes are administered to humans and animals to improve nutrition.

For example, in cases of lactose intolerance, preparations of lactase (such as Lactaid™) are administered to humans in need thereof. Lactose intolerance is characterized by gastrointestinal discomfort, including gas, bloating, crampls and diarrhea, after the consumption of milk or milk-containing products. The digestive enzymes of particular interest, for example in therapy in humans and animals, therefore also include lactase and functional mutants, variants and derivatives thereof.

Likewise, preparations of galactosidases (such as Beano™ or Nutritek™ Alpha Galactosidase) are administered to humans in need thereof. Such products improve digestion of sugars found in foods including legumes and cruciferous vegetables and reduce effects generally associated with the foods, such as gas and bloating.

Preparations of digestive enzymes that are prepared for human, veterinary, diagnostic and/or experimental use may contain unwanted and potentially dangerous biological contaminants or pathogens, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. Consequently, it is of utmost importance that any biological contaminant in the preparation be inactivated before the product is used. This is especially critical when the preparation is to be administered directly to a patient, for example in human therapy corrected or treated by intravenous, intramuscular or other forms of injection. This is also critical for the various preparations that are prepared in media or via culture of cells or recombinant cells which contain various types of plasma and/or plasma derivatives or other biological materials or are used to prepare biological materials for human use and which may be subject to mycoplasma, prion, bacterial, viral and/or other biological contaminants or pathogens.

Most procedures for producing preparations of digestive enzymes have involved methods that screen or test the preparation for one or more particular biological contaminants or pathogens rather than removal or inactivation of the contaminant(s) and/or pathogen(s) from the preparation. Preparations that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers, and in the case of as yet unknown viruses or other contaminants or pathogens that may be in blood. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the preparation is contaminated. Therefore, it would be desirable to apply techniques that would kill or inactivate biological contaminants and pathogens during and/or after manufacturing the preparation of digestive enzymes.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used.

In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses of concern for both human and animal-derived preparations, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

Heat treatment requires that the product be heated to approximately 60° C. for about 70 hours which can be damaging to sensitive products. In some instances, heat inactivation can actually destroy 50% or more of the biological activity of the product.

Filtration involves filtering the product in order to physically remove contaminants. Unfortunately, this method may also remove products that have a high molecular weight. Further, in certain cases, small viruses and similarly sized contaminants and pathogens, such as prions, may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al, "Is There Life After Irradiation? Part 2," *BioPharm* July-August, 1993, and Leitman, USe of Blood Cell Irradiation in the Prevention of Post Transfusion Graft-vs-Host Disease," *Transfusion Science* 10:219–239 (1989)). The published literature in this area, however, teaches that gamma radiation can be damaging to radiation sensitive products, such as blood, blood products, enzymes, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies (Mab), may lose viability and activity if subjected to freezing for irradiation purposes and then thawing prior to administration to a patient.

In view of the difficulties discussed above, there remains a need for methods of sterilizing preparations of one or more digestive enzymes that are effective for reducing the level of active biological contaminants or pathogens without an adverse effect on the preparation.

SUMMARY OF THE INVENTION

Accordingly, it is an object of the present invention to provide methods of sterilizing preparations of digestive enzymes by reducing the level of active biological contaminants or pathogens without adversely effecting the preparation. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for sterilizing a preparation of one or more digestive enzymes that is sensitive to radiation comprising irradiating the preparation of one or more digestive enzymes with radiation for a time effective to sterilize the material at a rate effective to sterilize the material and to protect the material from radiation.

Another embodiment of the present invention is directed to a method for sterilizing a preparation of one or more digestive enzymes that is sensitive to radiation comprising: (i) adding to a preparation of one or more digestive enzymes at least one stabilizer in an amount effective to protect the preparation of one or more digestive enzymes from radiation; and (ii) irradiating the preparation of one or more digestive enzymes with radiation at an effective rate for a time effective to sterilize the material.

Another embodiment of the present invention is directed to a method for sterilizing a preparation of one or more digestive enzymes that is sensitive to radiation comprising: (i) reducing the residual solvent content of a preparation of one or more digestive enzymes to a level effective to protect the preparation of one or more digestive enzymes from radiation; and (ii) irradiating the preparation of one or more digestive enzymes with radiation at an effective rate for a time effective to sterilize the preparation of one or more digestive enzymes.

Another embodiment of the present invention is directed to a method for sterilizing a preparation of one or more digestive enzymes that is sensitive to radiation comprising: (i) reducing the temperature of a preparation of one or more digestive enzymes to a level effective to protect the preparation of one or more digestive enzymes from radiation; and (ii) irradiating the preparation of one or more digestive enzymes with radiation at an effective rate for a time effective to sterilize the preparation of one or more digestive enzymes.

Another embodiment of the present invention is directed to a method for sterilizing a preparation of one or more digestive enzymes that is sensitive to radiation comprising: (i) applying to the preparation of one or more digestive enzymes a stabilizing process selected from the group consisting of: (a) reducing the residual solvent content of a preparation of one or more digestive enzymes, (b) adding to the preparation of one or more digestive enzymes at least one stabilizer, and (c) reducing the temperature of the preparation of one or more digestive enzymes; and (ii) irradiating the preparation of one or more digestive enzymes with radiation at an effective rate for a time effective to sterilize the preparation of one or more digestive enzymes, wherein the stabilizing process and the rate of irradiation are together effective to protect the preparation of one or more digestive enzymes from radiation.

Another embodiment of the present invention is directed to a method for sterilizing a preparation of one or more digestive enzymes that is sensitive to radiation comprising: (i) applying to the preparation of one or more digestive enzymes at least two stabilizing processes selected from the group consisting of: (a) reducing the residual solvent content of a preparation of one or more digestive enzymes, (b) adding to the preparation of one or more digestive enzymes at least one stabilizer, and (c) reducing the temperature of the preparation of one or more digestive enzymes; and (ii) irradiating the preparation of one or more digestive enzymes with radiation at an effective rate for a time effective to sterilize the preparation of one or more digestive enzymes, wherein the stabilizing processes may be performed in any order and are together effective to protect the preparation of one or more digestive enzymes from radiation.

The invention also provides a biological composition comprising at least one preparation of one or more digestive enzymes and a least one stabilizer in an amount effective to preserve the preparation of one or more digestive enzymes for its intended use following sterilization with radiation.

The invention also provides a biological composition comprising at least one preparation of one or more digestive enzymes in which the residual solvent content has been reduced to a level effective to preserve the preparation of one or more digestive enzymes for its intended use following sterilization with radiation.

The invention also provides a biological composition comprising at least one preparation of one or more digestive enzymes and at least one stabilizer in which the residual solvent content has been reduced and wherein the amount of stabilizer and level of residual solvent content are together effective to preserve the preparation of one or more digestive enzymes for its intended use following sterilization with radiation.

The invention also provides a biological composition comprising at least one preparation of one or more digestive enzymes wherein the total protein concentration of the preparation is effective to preserve the preparation of one or more digestive enzymes for its intended use following sterilization with radiation.

Figure 1A:
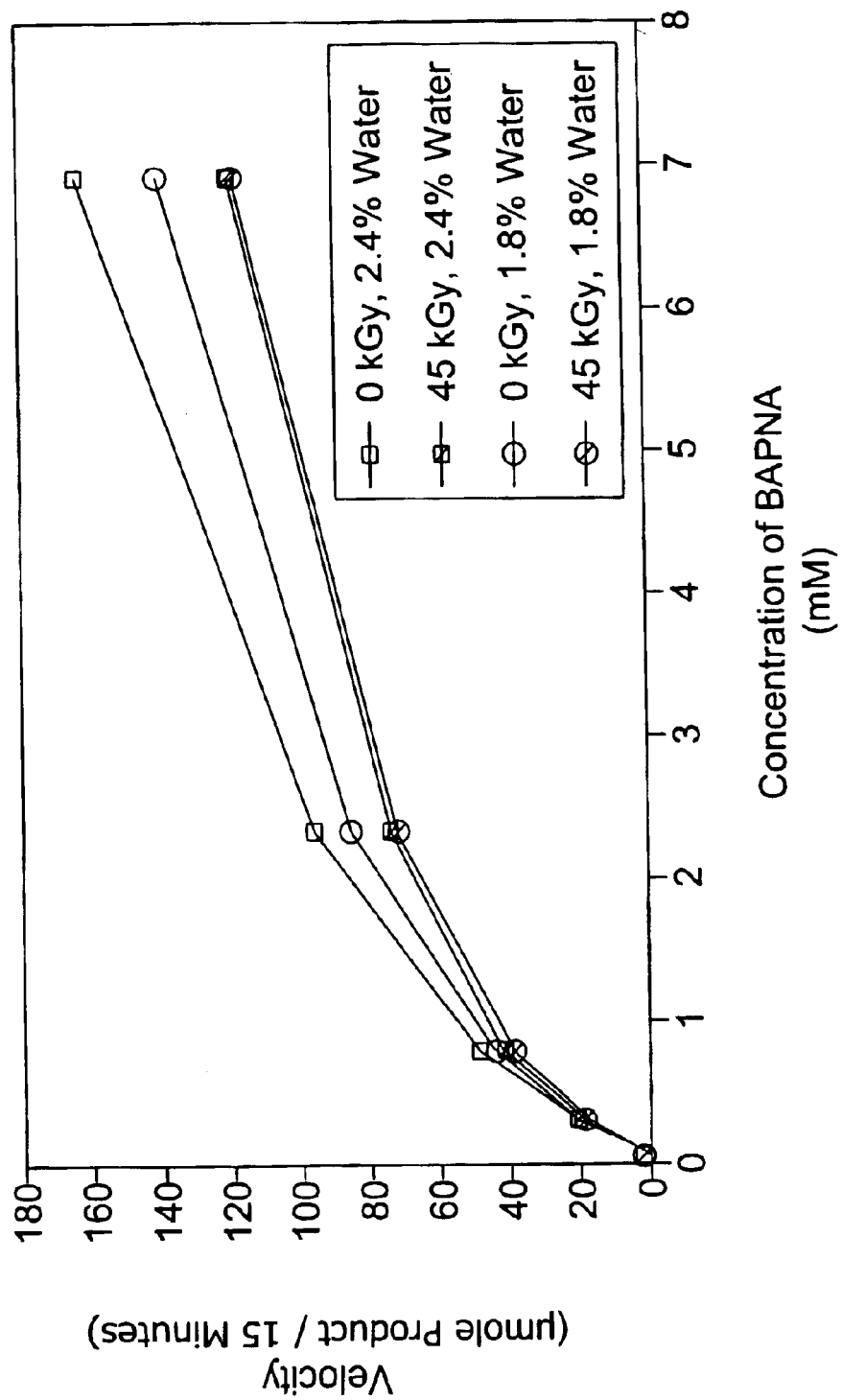
FIGS. 1A–1B are graphs showing the activity of lyophilized trypsin following gamma irradiation in the absence or presence of a stabilizer and at varying levels of residual solvent content.

FIGS, 11A–11C are gels showing the protective effect of ascorbate (200 mM) and a combination of ascorbate (200 mM) and Gly-Gly (200 mM) on a lyophilized glycosidase preparation.

DETAILED DESCRIPTION OF THE PREFERRED EMBODIMENTS

A. Definitions

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "preparation of one or more digestive enzymes" is intended to mean any preparation derived or obtained from a living organism that contains one or more of enzymes involved in the breakdown or conversion of one substance into a second substance, particularly protein(s), lipid(s) and/or cabohydrate(s). Illustrative examples of digestive enzymes include, but are not limited to, intracellular and intercellular enzymes produced by, present in or introduced into the digestive tract of any living organism, or involved in the metabolism, catabolism, storage and mobilization of externally or internally-derived nutrients or the breakdown products of tissue and/or cellular repair, regeneration, or removal, such as the following: pancreatic enzymes, including pancreatic proteolytic enzymes, such as trypsin and chymotrypsin, pancreatic lipase and pancreatic amylase; salivary enzymes, such as ptyalin; intestinal enzymes, including intestinal polypeptidases, intestinal amylases and intestinal lipases; glycosidases, such as α-galactosidase; and sulfatases, such as iduronodate-2-sulfatase.

As used herein, the term "sterilize" is intended to mean a reduction in the level of at least one active biological contaminant or pathogen found in the preparation being treated according to the present invention.

As used herein, the term "biological contaminant or pathogen" is intended to mean a contaminant or pathogen that, upon direct or indirect contact with a preparation of one or more digestive enzymes, may have a deleterious effect on the digestive enzymes or upon a recipient thereof. Such biological contaminants or pathogens include the various viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites known to those of skill in the art to generally be found in or infect preparations of digestive enzymes. Examples of biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C), pox viruses, toga viruses, Epstein-Barr viruses and parvoviruses; bacteria, such as Escherichia, Bacillus, Campylobacter, Streptococcus and Staphalococcus; nanobacteria; parasites, such as Trypanosoma and malarial parasites, including Plasmodium species; yeasts; molds; mycoplasmas and ureaplasmas; chlamydia; rickettsias, such as *Coxiella burnetti*; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease); Creutzfeld-Jakob disease (including variant or new variant CJD), Fatal Familial Insomnia; Gerstmann-Straeussler-Scheinker syndrome; kuru; and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the preparation of digestive enzymes and/or a recipient thereof.

As used herein, the term "a biologically compatible solution" is intended to mean a solution to which a preparation of one or more digestive enzymes may be exposed, such as by being suspended or dissolved therein, and remain viable, i.e., retain its essential biological and physiological characteristics.

As used herein, the term "a biologically compatible buffered solution" is intended to mean a biologically compatible solution having a pH and osmotic properties (e.g., tonicity, osmolality and/or oncotic pressure) suitable for maintaining the integrity of the material(s) therein. Suitable biologically compatible buffered solutions typically have a pH between 4 and 8.5 and are isotonic or only moderately hypotonic or hypertonic. Biologically compatible buffered solutions are known and readily available to those of skill in the art.

As used herein, the term "stabilizer" is intended to mean a compound or material that reduces damage to the biological material being irradiated to a level that is insufficient to preclude the safe and effective use of the material. Illustrative examples of stabilizers include, but are not limited to, the following: antioxidants; free radical scavengers, including spin traps; combination stabilizers, i.e. stabilizers which are effective at quenching both Type I and Type II photodynamic reactions; and ligands, such as heparin, that stabilize the molecules to which they bind. Preferred examples of stabilizers include, but are not limited to, the following: ethanol; acetone; fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6, 8-dithioloctanoic acid methyl ester), lipoamide, bisonor methyl ester and tatranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalose; amino acids and derivatives thereof, such as histidine, N-acetylcysteine (NAC), glutamic acid, tryptophan, sodium caprylate, N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and reduced glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (MOPS); 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); proteins and peptides, such as glycylglycine and camosine, in which each amino acid may be in its D or L form; diosmin; pupurogalin; gallic acid and its derivatives including but not limited to propyl gallate, sodium formaldehyde sulfoxylate and silymarin. Particularly preferred examples include single stabilizers or combinations of stabilizers that are effective at quenching both Type I and Type II photodynamic reactions and volatile stabilizers, which can be applied as a gas and/or easily removed by evaporation, low pressure and similar methods.

As used herein, the term "residual solvent content" is intended to mean the amount or proportion of freely available liquid in the preparation of one or more digestive enzymes. Freely available liquid means the liquid, such as water or an organic solvent (e.g. ethanol, isopropanol, acetone, polyethylene glycol, etc.), present in the preparation being sterilized that is not bound to or complexed with one or more of the non-liquid components of the preparation. Freely available liquid includes intracellular water. The residual solvent contents related as water referenced herein refer to levels determined by the FDA approved, modified Karl Fischer method (Meyer and Boyd, *Analytical Chem.*, 31:215–219, 1959; May, et al., *J. Biol. Standardization*, 10:249–259, 1982; Centers for Biologics Evaluation and Research, FDA, Docket No. 89D-0140, 83–93; 1990) and/or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viral, bacterial, nanobacterial, mold, yeast, fungal, prion and/or parasitic contaminants or pathogens, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactives and their derivatives and analogs; angelicins, khellins and coumarins which contain a halogen substituent and a water solubilization moiety, such as quaternary ammonium ion or phosphonium ion; nucleic acid binding compounds; brominated hematoporphyrin; phthalocyanines; purpurins; porphorins; halogenated or metal atom-substituted derivatives of dihematoporphyrin esters, hematoporphyrin derivatives, benzoporphyrin derivatives, hydrodibenzoporphyrin dimaleimade, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide.

As used herein, the term "radiation" is intended to mean radiation of sufficient energy to sterilize at least some component of the irradiated preparation of one or more digestive enzymes. Types of radiation include, but are not limited to, the following: (i) corpuscular (streams of subatomic particles such as neutrons, electrons, and/or protons); and (ii) electromagnetic (originating in a varying electromagnetic field, such as radio waves, visible (both mono and polychromatic) and invisible light, infrared, ultraviolet radiation, x-radiation, and gamma rays and mixtures thereof). Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while X-rays are produced by machines that emit X-radiation, and electrons are often used to sterilize materials in a method known as "E-beam" irradiation that involves their production via a machine.

As used herein, the term "to protect" is intended to mean to reduce any damage to the preparation of one or more digestive enzymes being irradiated, that would otherwise result from the irradiation of that material, to a level that is insufficient to preclude the safe and effective use of the material following irradiation. In other words, a substance or process "protects" a preparation of one or more digestive enzymes from radiation if the presence of that substance or carrying out that process results in less damage to the material from irradiation than in the absence of that substance or process. Thus, a preparation of one or more digestive enzymes may be used safely and effectively after irradiation in the presence of a substance or following performance of a process that "protects" the material, but could not be used safely and effectively after irradiation under identical conditions but in the absence of that substance or the performance of that process.

B. Particularly Preferred Embodiments

A first preferred embodiment of the present invention is directed to a method for sterilizing a preparation of one or more digestive enzymes that is sensitive to radiation comprising irradiating the preparation of one or more digestive enzymes with radiation for a time effective to sterilize the material at a rate effective to sterilize the material and to protect the material from radiation.

Another preferred embodiment of the present invention is directed to a method for sterilizing a preparation of one or more digestive enzymes that is sensitive to radiation comprising: (i) adding to a preparation of one or more digestive enzymes at least one stabilizer in an amount effective to protect the preparation of one or more digestive enzymes from radiation; and (ii) irradiating the preparation of one or more digestive enzymes with radiation at an effective rate for a time effective to sterilize the material.

Another preferred embodiment of the present invention is directed to a method for sterilizing a preparation of one or more digestive enzymes that is sensitive to radiation comprising: (i) reducing the residual solvent content of a preparation of one or more digestive enzymes to a level effective to protect the preparation of one or more digestive enzymes from radiation; and (ii) irradiating the preparation of one or more digestive enzymes with radiation at an effective rate for a time effective to sterilize the preparation of one or more digestive enzymes.

Another preferred embodiment of the present invention is directed to a method for sterilizing a preparation of one or more digestive enzymes that is sensitive to radiation comprising: (i) reducing the temperature of a preparation of one or more digestive enzymes to a level effective to protect the preparation of one or more digestive enzymes from radiation; and (ii) irradiating the preparation of one or more digestive enzymes with radiation at an effective rate for a time effective to sterilize the preparation of one or more digestive enzymes.

Another preferred embodiment of the present invention is directed to a method for sterilizing a preparation of one or more digestive enzymes that is sensitive to radiation comprising: (i) applying to the preparation of one or more digestive enzymes a stabilizing process selected from the group consisting of: (a) reducing the residual solvent content of a preparation of one or more digestive enzymes, (b) adding to the preparation of one or more digestive enzymes at least one stabilizer, and (c) reducing the temperature of the preparation of one or more digestive enzymes; and (ii) irradiating the preparation of one or more digestive enzymes with radiation at an effective rate for a time effective to sterilize the preparation of one or more digestive enzymes, wherein the stabilizing process and the rate of irradiation are together effective to protect the preparation of one or more digestive enzymes from radiation.

Another preferred embodiment of the present invention is directed to a method for sterilizing a preparation of one or more digestive enzymes that is sensitive to radiation comprising: (i) applying to the preparation of one or more digestive enzymes at least two stabilizing processes selected from the group consisting of: (a) reducing the residual solvent content of a preparation of one or more digestive enzymes, (b) adding to the preparation of one or more digestive enzymes at least one stabilizer, and (c) reducing the temperature of the preparation of one or more digestive enzymes; and (ii) irradiating the preparation of one or more digestive enzymes with radiation at an effective rate for a time effective to sterilize the preparation of one or more digestive enzymes, wherein the stabilizing processes may be performed in any order and are together effective to protect the preparation of one or more digestive enzymes from radiation.

According to certain methods of the present invention, a stabilizer is added to the preparation of one or more digestive enzymes prior to irradiation of the preparation of one or more digestive enzymes with radiation. This stabilizer is added in an amount that is effective to protect the preparation of one or more digestive enzymes from the radiation. Suitable amounts of stabilizer may vary depending upon certain features of the particular method(s) of the present invention being employed, such as the nature and characteristics of the particular preparation of one or more digestive enzymes and/or stabilizer being used, and/or the intended use of the preparation of one or more digestive enzymes being irradiated, and can be determined empirically by one skilled in the art.

According to certain methods of the present invention, the residual solvent content of the preparation of one or more digestive enzymes is reduced prior to irradiation of the preparation of one or more digestive enzymes with radiation. The residual solvent content is reduced to a level that is effective to protect the preparation of one or more digestive enzymes from the radiation. Suitable levels of residual solvent content may vary depending upon certain features of the particular method(s) of the present invention being employed, such as the nature and characteristics of the particular preparation of one or more digestive enzymes and/or stabilizer being used, and/or the intended use of the preparation of one or more digestive enzymes being irradiated, and can be determined empirically by one skilled in the art. There may be preparations for which it is desirable to maintain the residual solvent content to within a particular range, rather than a specific value, for example when the solvent, or at least one of the solvents in a mixture, is also a stabilizer, such as an alcohol (e.g. ethanol) or dialkyl ketone (e.g. acetone).

When the solvent is water, and particularly when the preparation of one or more digestive enzymes is in a solid phase, the residual solvent content is generally less than about 15%, typically less than about 10%, more typically less than about 9%, even more typically less than about 8%, usually less than about 5%, preferably less than about 3.0%, more preferably less than about 2.0%, even more preferably less than about 1.0%, still more preferably less than about 0.5%, still even more preferably less than about 0.2% and most preferably less than about 0.08%.

The solvent may preferably be a non-aqueous solvent, more preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In certain embodiments of the present invention, the solvent may be a mixture of water and a non-aqueous solvent or solvents, such as ethanol and/or acetone. In such embodiments, the non-aqueous solvent(s) is preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In a preferred embodiment, when the residual solvent is water, the residual solvent content of a biological material is reduced by dissolving or suspending the biological material in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

When the biological material is in a liquid phase, reducing the residual solvent content may be accomplished by any of a number of means, such as by increasing the solute concentration. In this manner, the concentration of the biological material dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular biological material may be found to lie within a range, rather than at a specific point. Such a range for the preferred residual solvent content of a particular biological material may be determined empirically by one skilled in the art.

While not wishing to be bound by any theory of operability, it is believed that the reduction in residual solvent content reduces the degrees of freedom of the preparation of one or more digestive enzymes, reduces the number of targets for free radical generation and may restrict the solubility or diffusion of these free radicals. Similar results might therefore be achieved by lowering the temperature of the preparation of one or more digestive enzymes below its eutectic point or below its freezing point, or by vitrification to likewise reduce the degrees of freedom of the preparation of one or more digestive enzymes. These results may permit the use of a higher rate and/or dose of radiation than might otherwise be acceptable. Thus, the methods described herein may be carried out at any temperature that doesn't result in an unacceptable level of damage to the preparation. Preferably, the methods described herein are performed at ambient temperature or below ambient temperature, such as below the eutectic point or freezing point of the preparation of one or more digestive enzymes being irradiated.

In accordance with the methods of the present invention, an "acceptable level" of damage may vary depending upon certain features of the particular method(s) of the present invention being employed, such as the nature and characteristics of the particular preparation of one or more digestive enzymes and/or stabilizer being used, and/or the intended use of the preparation of one or more digestive enzymes being irradiated, and can be determined empirically by one skilled in the art. An "unacceptable level" of damage would therefore be a level of damage that would preclude the safe and effective use of the preparation of one or more digestive enzymes being sterilized. The particular level of damage in a given preparation of one or more digestive enzymes may be determined using any of the methods and techniques known to one skilled in the art.

The residual solvent content of a preparation of one or more digestive enzymes may be reduced by any of the methods and techniques known to those skilled in the art for reducing solvent from a preparation of one or more digestive enzymes without producing an unacceptable level of damage to the preparation. Such methods include, but are not limited to, evaporation, concentration, centrifugal concentration, vitrification, addition of solute, lyophilization (with or without the prior addition of ascorbate) and spray-drying.

A particularly preferred method for reducing the residual solvent content of a preparation of one or more digestive enzymes is lyophilization, even more preferred is lyophilization following the addition of ascorbate.

Another particularly preferred method for reducing the residual solvent content of a preparation of one or more digestive enzymes is vitrification, which may be accomplished by any of the methods and techniques known to those skilled in the art, including the addition of solute and or additional solutes, such as sucrose, to raise the eutectic point of the biological material, followed by a gradual application of reduced pressure to the biological material in order to remove the residual solvent, such as water. The resulting glassy material will then have a reduced residual solvent content.

According to certain methods of the present invention, the preparation of one or more digestive enzymes to be sterilized may be immobilized upon a solid surface by any means known and available to one skilled in the art. For example, the preparation of one or more digestive enzymes to be sterilized may be present as a coating or surface on a biological or non-biological substrate.

The radiation employed in the methods of the present invention may be any radiation effective for the inactivation of one or more biological contaminants or pathogens of the preparation of one or more digestive enzymes being treated. The radiation may be corpuscular, including E-beam radiation. Preferably the radiation is electromagnetic radiation, including visible light, infrared, x-radiation, UV light and mixtures of various wavelengths of electromagnetic radiation. A particularly preferred form of radiation is gamma radiation.

According to the methods of the present invention, the preparation of one or more digestive enzymes to be sterilized is irradiated with the radiation at a rate effective for the inactivation of one or more biological contaminants or pathogens of the preparation. Suitable rates of irradiation may vary depending upon certain features of the methods of the present invention being employed, such as the nature and characteristics of the particular preparation of one or more digestive enzymes being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low ($\leq 3$ kGy/hour) and high (>3 kGy/hour) rates may be utilized in the methods described herein to achieve such results.

According to a particularly preferred embodiment of the present invention, the rate of irradiation is not more than about 3.0 kGy/hour, more preferably between about 0.1 kGy/hr. and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr., more preferably at least about 6 kGy/hr., even more preferably at least about 16 kGy/hr., and even more preferably at least about 30 kGy/hr and most preferably at least about 45 kGy/hr or greater.

According to the methods of the present invention, the preparation of one or more digestive enzymes to be sterilized is irradiated with the radiation for a time effective for the inactivation of one or more biological contaminants or pathogens of the preparation of one or more digestive enzymes. Combined with irradiation rate, the appropriate irradiation time results in the appropriate dose of irradiation being applied to the preparation of one or more digestive enzymes. Suitable irradiation times may vary depending upon the particular form and rate of radiation involved, the nature and characteristics of the particular preparation of one or more digestive enzymes being irradiated and/or the particular biological contaminants or pathogens being inactivated. Suitable irradiation times can be determined empirically by one skilled in the art.

According to the methods of the present invention, the preparation of one or more digestive enzymes to be sterilized is irradiated with radiation up to a total dose effective for the inactivation of one or more active biological contaminants or pathogens in the material, while not producing an unacceptable level of damage to that material. Suitable total doses of radiation may vary depending upon certain features of the methods of the present invention being employed, such as the nature and characteristics of the particular preparation being irradiated, the particular form of radiation involved and/or the particular active biological contaminant or pathogen being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the preparation of one or more digestive enzymes being irradiated, such as the thickness and distance from the source of radiation, may be determined empirically by one skilled in the art.

According to certain methods of the present invention, an effective amount of at least one sensitizing compound may optionally be added to the preparation of one or more digestive enzymes prior to irradiation, for example to enhance the effect of the irradiation on the biological contaminant(s) or pathogen(s) therein, while employing the methods described herein to minimize the deleterious effects of irradiation upon the preparation of one or more digestive enzymes. Suitable sensitizers are known to those skilled in the art, and include, for example, psoralens and their derivatives and analogs and inactines and their derivatives and analogs.

According to the methods of the present invention, the irradiation of the preparation of one or more digestive enzymes may occur at any temperature that is not deleterious to the preparation of one or more digestive enzymes being sterilized. According to one preferred embodiment, the preparation of one or more digestive enzymes is irradiated at ambient temperature. According to an alternate preferred embodiment, the preparation of one or more digestive enzymes is irradiated at reduced temperature, i.e. a temperature below ambient temperature, such as 0° C., −20° C., −40° C., −60° C., −78° C. or −196° C. According of the present invention, the preparation of one or more digestive enzymes is preferably irradiated at or below the freezing or eutectic point of the preparation of one or more digestive enzymes. According to another alternate preferred embodiment, the preparation of one or more digestive enzymes is irradiated at elevated temperature, i.e. a temperature above ambient temperature, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the preparation of one or more digestive enzymes occurs at a temperature that protects the preparation from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular preparation of one or more digestive enzymes may be determined empirically by one skilled in the art.

According to the methods of the present invention, the irradiation of the preparation of one or more digestive enzymes may occur at any pressure which is not deleterious to the biological material being sterilized. According to one preferred embodiment, the preparation of one or more digestive enzymes is irradiated at elevated pressure. More preferably, the preparation of one or more digestive enzymes is irradiated at elevated pressure due to the application of sound waves, the use of a volatile, compression or other means known to those skilled in the art. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to the methods of the present invention, the pH of the preparation of one or more digestive enzymes undergoing sterilization is about 7. In some embodiments of the present invention, however, the preparation of one or more digestive enzymes may have a pH of less than 7, preferably less than or equal to 6, more preferably less than or equal to 5, even more preferably less than or equal to 4, and most preferably less than or equal to 3. In alternative embodiments of the present invention, the preparation of one or more digestive enzymes may have a pH of greater than 7, preferably greater than or equal to 8, more preferably greater than or equal to 9, even more preferably greater than or equal to 10, and most preferably greater than or equal to 11. According to certain embodiments of the present invention, the pH of the preparation undergoing sterilization is at or near the isoelectric point of the enzyme(s) contained in the preparation. According to other embodiments of the present invention, the pH of the preparation undergoing sterilization is at or near the pH at which at least one enzyme in the preparation has maximal affinity for its substrate(s). Suitable pH levels can be determined empirically by one skilled in the art.

Similarly, according to the methods of the present invention, the irradiation of the preparation of one or more digestive enzymes may occur under any atmosphere that is not deleterious to the preparation of one or more digestive enzymes being treated. According to one preferred embodiment, the preparation of one or more digestive enzymes is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the preparation of one or more digestive enzymes is held under vacuum while being irradiated. According to a particularly preferred embodiment of the present invention, a preparation of one or more digestive enzymes (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid preparation of one or more digestive enzymes is held under low pressure, to decrease the amount of gas, particularly oxygen, dissolved in the liquid, prior to irradiation, either with or without a prior step of solvent reduction, such as lyophilization. Such degassing may be performed using any of the methods known to one skilled in the art.

In another preferred embodiment, where the preparation of one or more digestive enzymes contains oxygen or other gases dissolved within or associated with it, the amount of these gases within or associated with the preparation may be reduced by any of the methods and techniques known and available to those skilled in the art, such as the controlled reduction of pressure within a container (rigid or flexible) holding the preparation to be treated or by placing the preparation in a container of approximately equal volume.

It will be appreciated that the combination of one or more of the features described herein may be employed to further minimize undesirable effects upon the preparation of one or more digestive enzymes caused by irradiation, while maintaining adequate effectiveness of the irradiation process on the biological contaminant(s) or pathogen(s). For example, in addition to the use of a stabilizer, a particular preparation of one or more digestive enzymes may also be lyophilized, held at reduced temperature and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. The desirable components of a preparation of one or more digestive enzymes may also be considered to have a $D_{37}$ value equal to the dose of radiation required to eliminate all but 37% of their desirable biological and physiological characteristics.

In accordance with certain preferred methods of the present invention, the sterilization of a preparation of one or more digestive enzymes is conducted under conditions that result in a decrease in the $D_{37}$ value of the biological contaminant or pathogen without a concomitant decrease in the $D_{37}$ value of the preparation of one or more digestive enzymes. In accordance with other preferred methods of the present invention, the sterilization of a preparation of one or more digestive enzymes is conducted under conditions that result in an increase in the $D_{37}$ value of the preparation of one or more digestive enzymes. In accordance with the most preferred methods of the present invention, the sterilization of a preparation of one or more digestive enzymes is conducted under conditions that result in a decrease in the $D_{37}$ value of the biological contaminant or pathogen and a concomitant increase in the $D_{37}$ value of the preparation of one or more digestive enzymes.

EXAMPLES

The following examples are illustrative, but not limiting, of the present invention. Other suitable modifications and adaptations are of the variety normally encountered by those skilled in the art and are fully within the spirit and scope of the present invention. Unless otherwise noted, all irradiation was accomplished using a $^{60}$Co source.

Example 1

In this experiment, lyophilized trypsin was irradiated (45 kGy at 1.9 kGy/hr) alone or in the presence of a stabilizer (sodium ascorbate 100 mM) at varying levels of residual solvent content.
Method
1 ml aliquots of trypsin alone or with 100 mM sodium ascorbate (10 mg/ml) were placed in 3 ml vials. Samples were prepared in triplicate and subjected to lyophilization, either a primary drying cycle (22 hours, sample temp 0–10° C., shelf temp 35° C., 10 mT) or a combination of a primary drying cycle and a secondary drying cycle (60 hours, sample temp 40° C., shelf temp 40° C., 10 mT).

All samples were resuspended in 1 ml water, and then diluted 1:10 for assay. Assay conditions: 50 units/ml trypsin per well+BAPNA substrate starting at 3000 µg/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).
Results In the absence of stabilizer, lyophilized trypsin exposed to 45 kGy total dose gamma-irradiation showed recovery of 74% of control activity at the higher residual solvent content level, i.e. about 2.4% water, and recovery of 85% of control activity at the lower residual solvent content level, i.e., about 1.8% water.

In the presence of stabilizer, trypsin exposed to 45 kGy total dose gamma-irradiation showed recovery of 97% of control activity at higher residual solvent content levels, i.e. about 3.7% water, and recovery of 86% of control activity at lower residual solvent content levels, i.e. about 0.7% water.

Figure 1B:
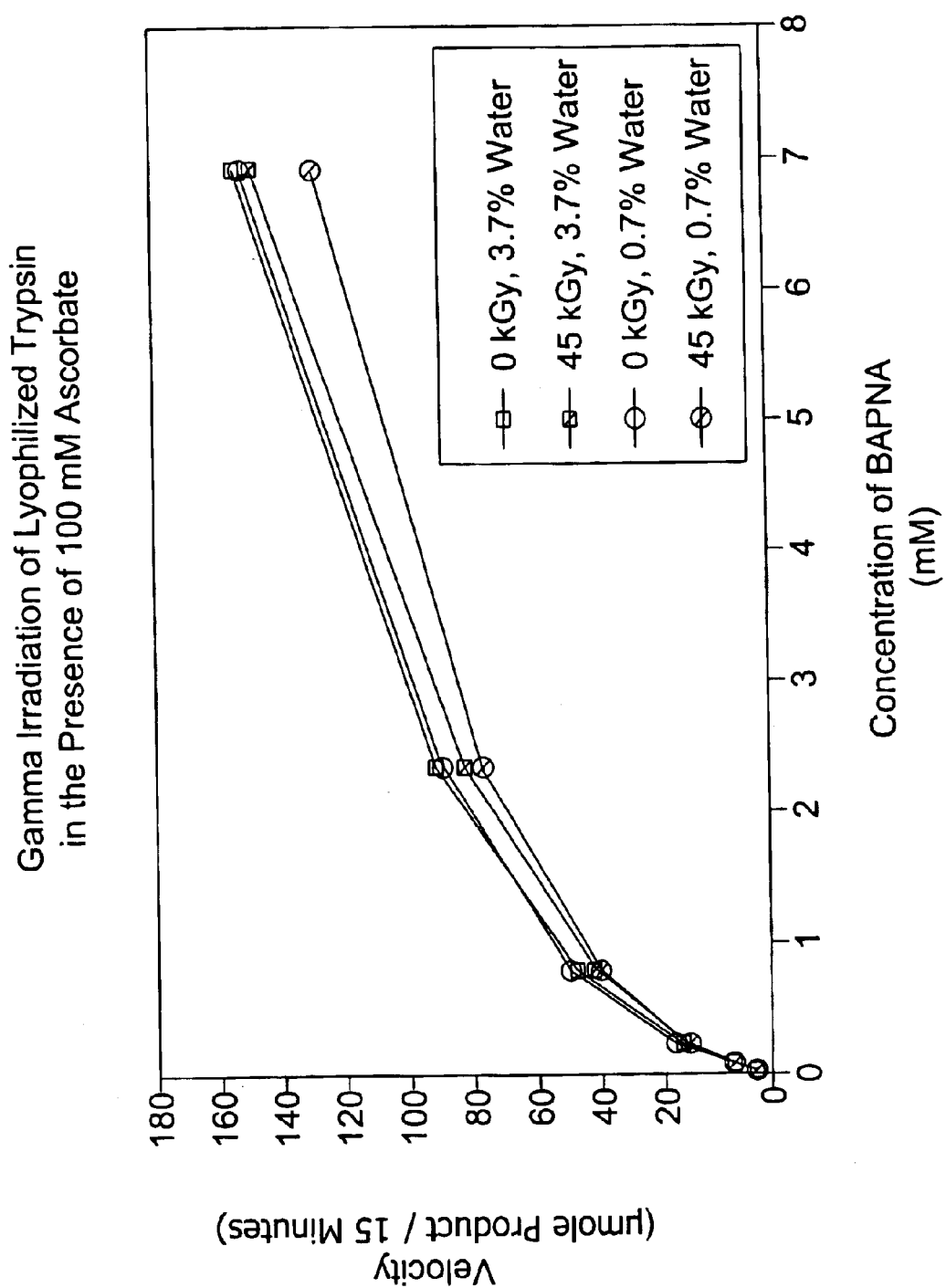

The results of this experiment are shown graphically in FIGS. 1A-1B.

Example 2

In this experiment, trypsin was irradiated (45 kGy at 1.6 kGy/hr. and 4° C.) in the presence of a stabilizer (sodium ascorbate 200 mM) as either a liquid or lyophilized preparation at varying pH levels.
Method
1 ml of 1 mg/ml (about 3000 IU/ml) trypsin aliquots in the presence of 35 mM phosphate buffer and 200 mM sodium ascorbate were made at varying pH levels between 5 and 8.5, inclusive. 400 µl of each solution was placed in 3 ml vials and then lyophilized and gamma-irradiated. The remaining portion of each solution was gamma-irradiated as a liquid. Lyophilized and liquid samples were assayed at the same time, under the following conditions: Assay conditions: 5 U/well trypsin (50 U/ml)+BATNA substrate (1 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).
Results Liquid trypsin samples exposed to 45 kGy total dose gamma-irradiation showed recovery of between about 70 and 75% of control activity across the pH range tested. Lyophilized trypsin samples showed recovery of between about 86 and 97% of control activity across the same pH ranges. More specifically, the following results were observed:

| Sample # | pH | lyophilized (% of control activity) | liquid (% of control activity) |
|---|---|---|---|
| 1 | 5 | 91.11 | 69.87 |
| 2 | 5.5 | 94.38 | 74.86 |
| 3 | 6 | 85.54 | 75.77 |
| 4 | 6.47 | 96.26 | 71.79 |
| 5 | 7 | 90.40 | 75.59 |
| 6 | 7.5 | 96.79 | 75.63 |
| 7 | 7.8 | 90.62 | 74.55 |
| 8 | 8.5 | 89.59 | 71.08 |

Figure 2:
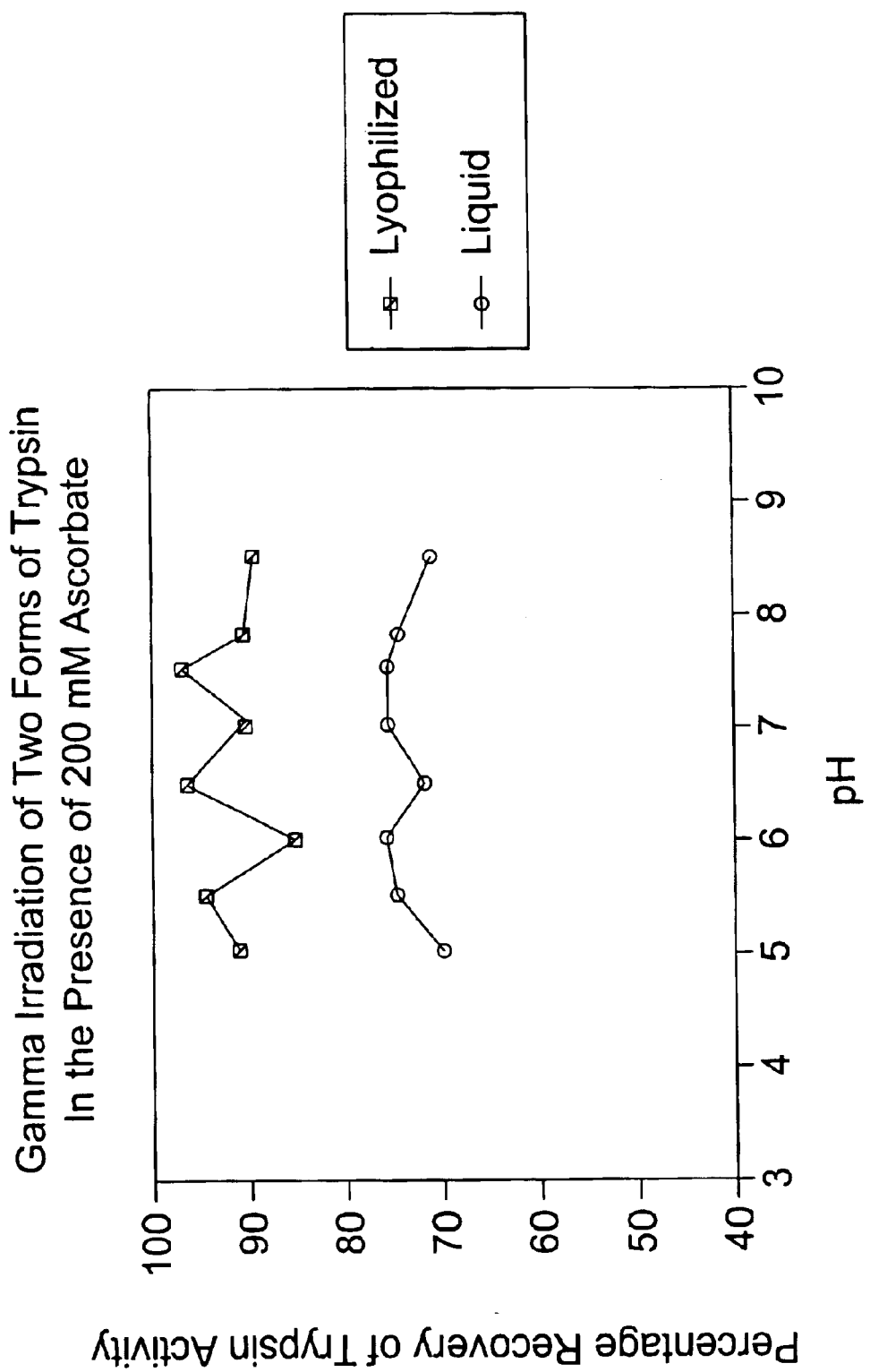
FIG. 2 is a graph showing the activity of liquid or lyophilized trypsin following gamma irradiation in the presence of a stabilizer and at varying pH levels.

The results of this experiment are shown graphically in FIG. 2.

Example 3

In this experiment, lyophilized trypsin was irradiated (42.7–44.8 kGy at 2.65 kGy/hr at 4° C.) alone or in the presence of a stabilizer (sodium ascorbate 200 mM).
Method
1 ml aliquots of trypsin alone or with 200 mM sodium ascorbate (1 mg/ml) were placed in 3 ml vials and frozen overnight at −70° C. Samples were prepared in quadruplicate and subjected to lyophilization, utilizing primary and secondary drying cycles (20 hours total).

Figure 3A:
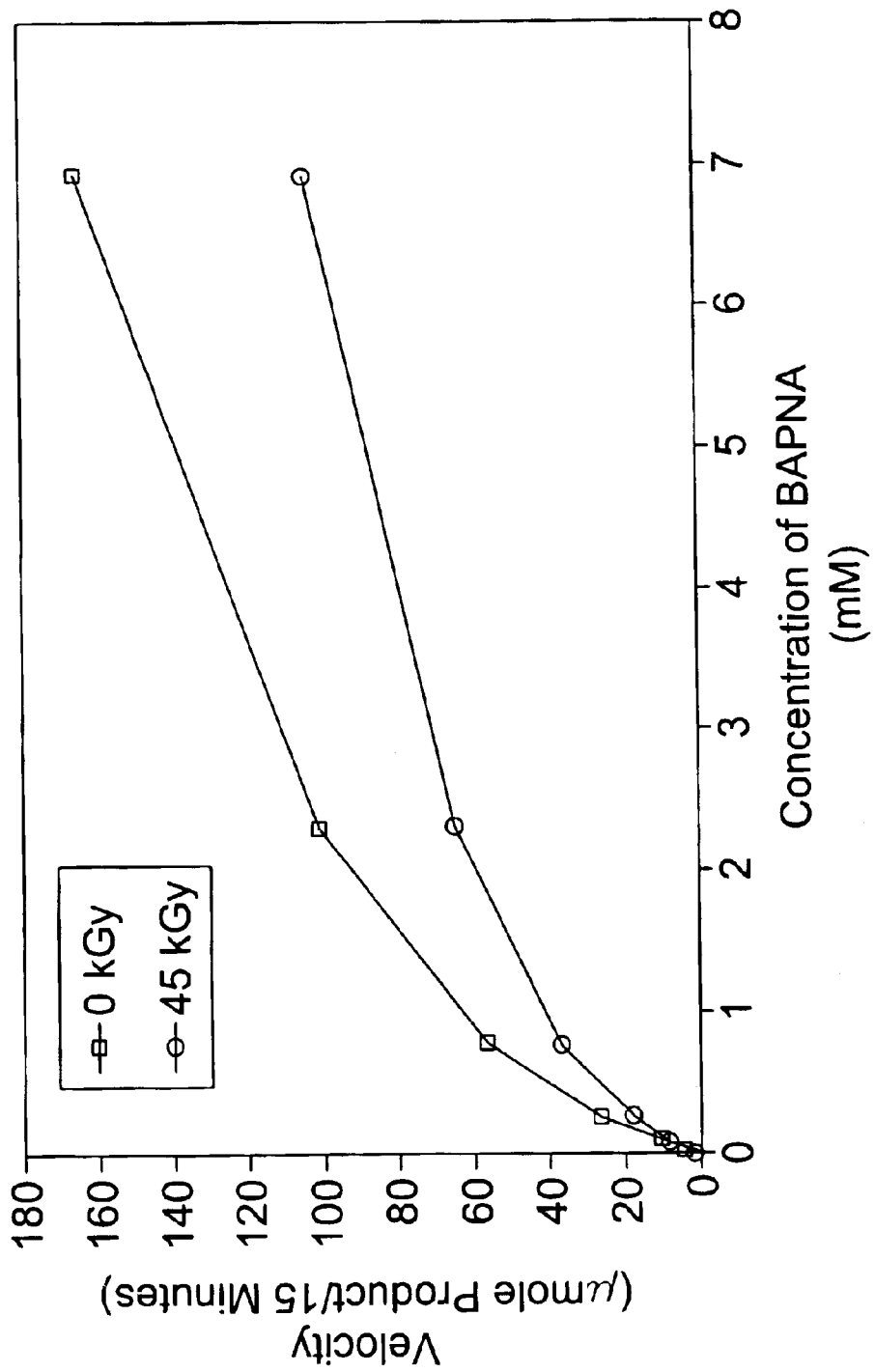
FIGS. 3A–3B are graphs showing the activity of lyophilized trypsin following gamma irradiation in the absence or presence of a stabilizer.
Figure 3B:
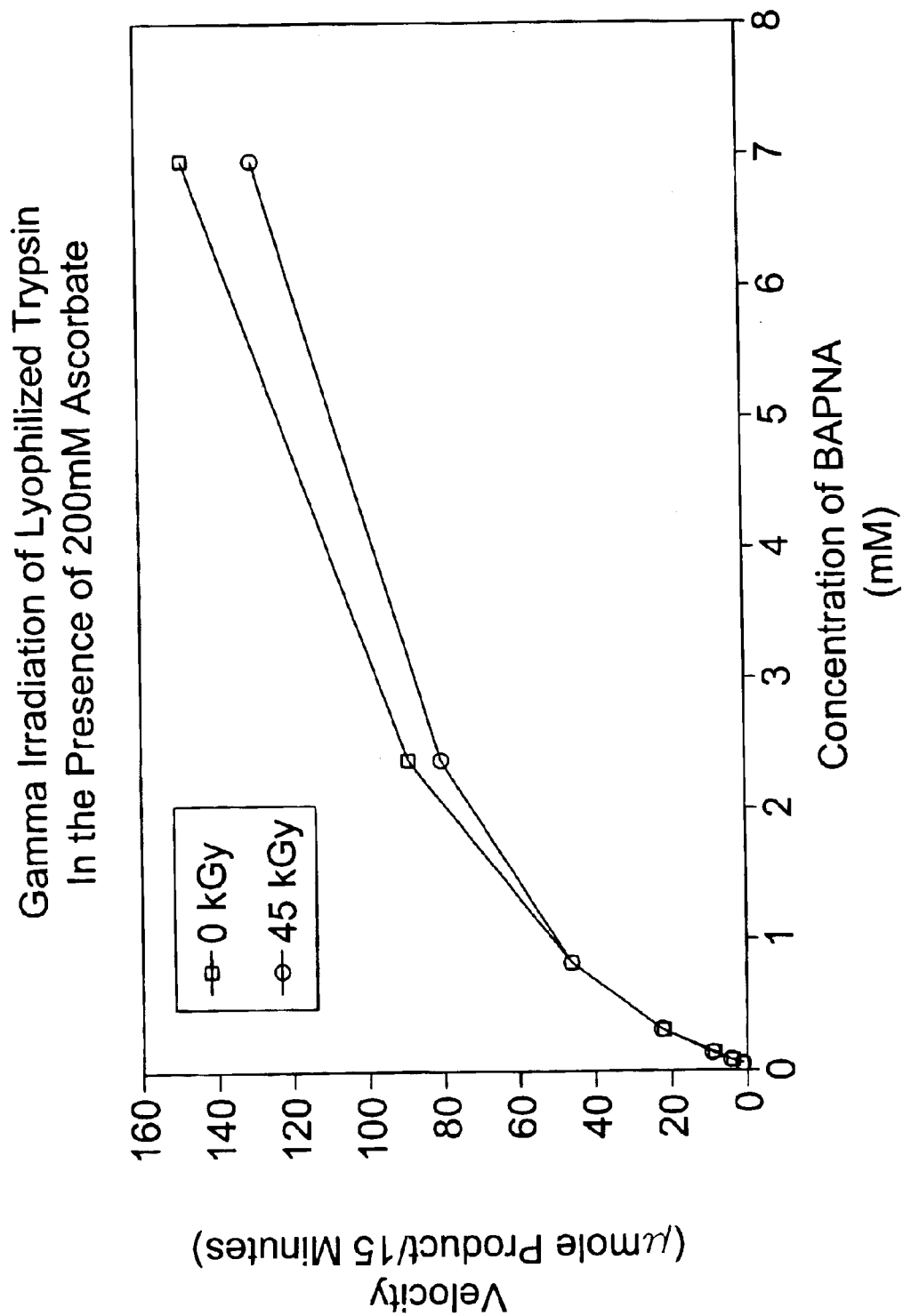

All samples were resuspended in 1 ml water, and then diluted 1:10 for assay. Assay conditions: 50 units/ml trypsin per well+BATNA substrate starting at 3000 µg/ml was serially diluted 3-fold down a 96-well plate. The assay was set up in two 96-well plates and absorption read at both 405 and 620 mn at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).
Results In the absence of stabilizer, lyophilized trypsin exposed to gamma-irradiation showed recovery of 63% of control activity. In the presence of stabilizer, lyophilized trypsin exposed to gamma-irradiation showed recovery of 88% of control activity. The results of this experiment are shown graphically in FIGS. 3A–3B.

Example 4

In this experiment, trypsin that had been lyophilized (0.7% moisture) was irradiated (45 kGy at 1.867 kGy/hr at 3.2° C.) alone or in the presence of a stabilizer (sodium ascorbate 100 mM) at varying levels of residual solvent content.
Method 1 ml aliquots of trypsin alone or with 100 mM sodium ascorbate (10 mg/ml) were placed in 3 ml vials and frozen overnight at −70° C. Samples were prepared in quadruplicate and subjected to lyophilization (69.5 hours total run time; shelf temperature 35° C.).

Figure 4A:
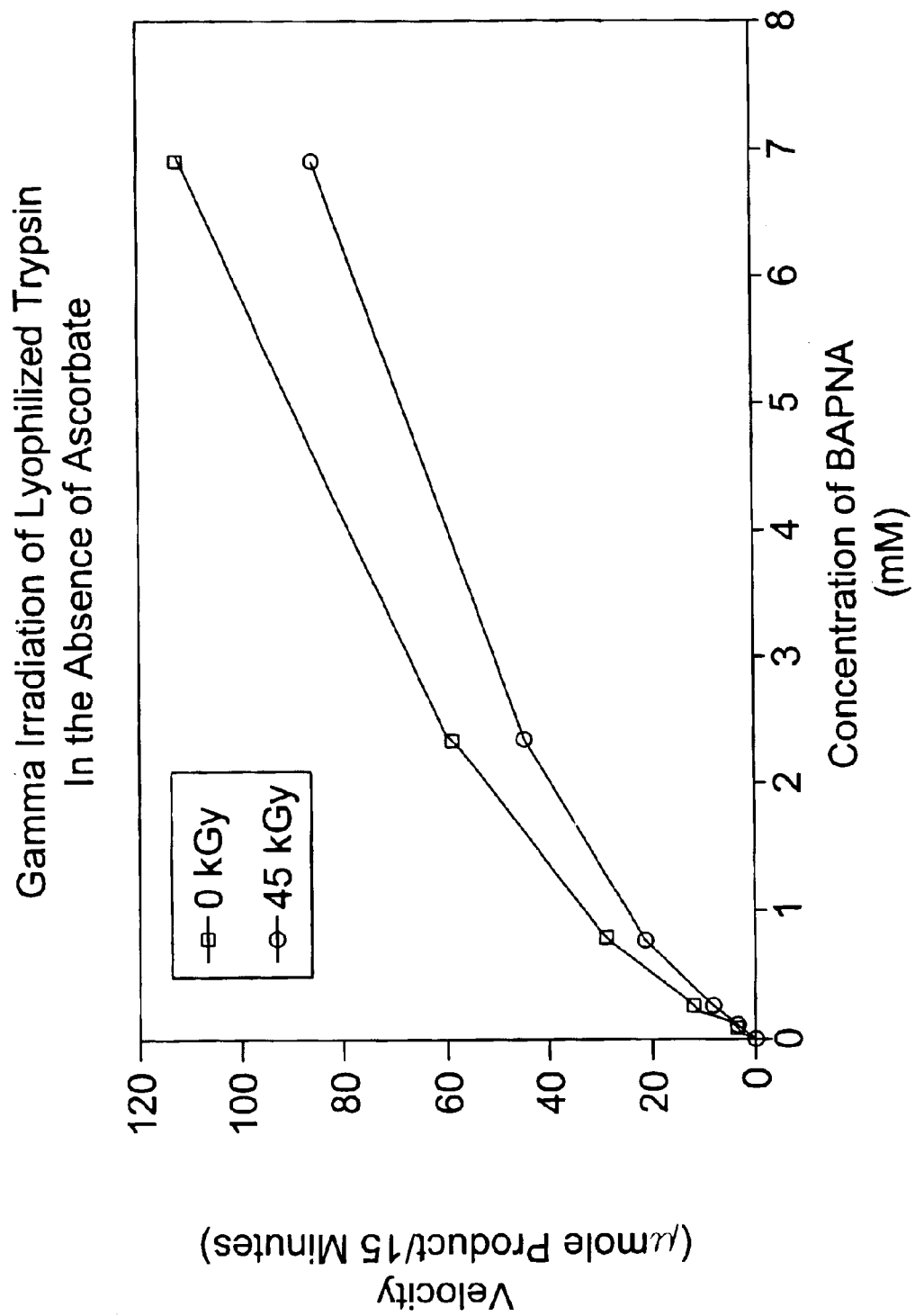
FIGS. 4A–4B are graphs showing the activity of lyophilized trypsin following gamma irradiation in the absence or presence of a stabilizer and at varying levels of residual solvent content.
Figure 4B:
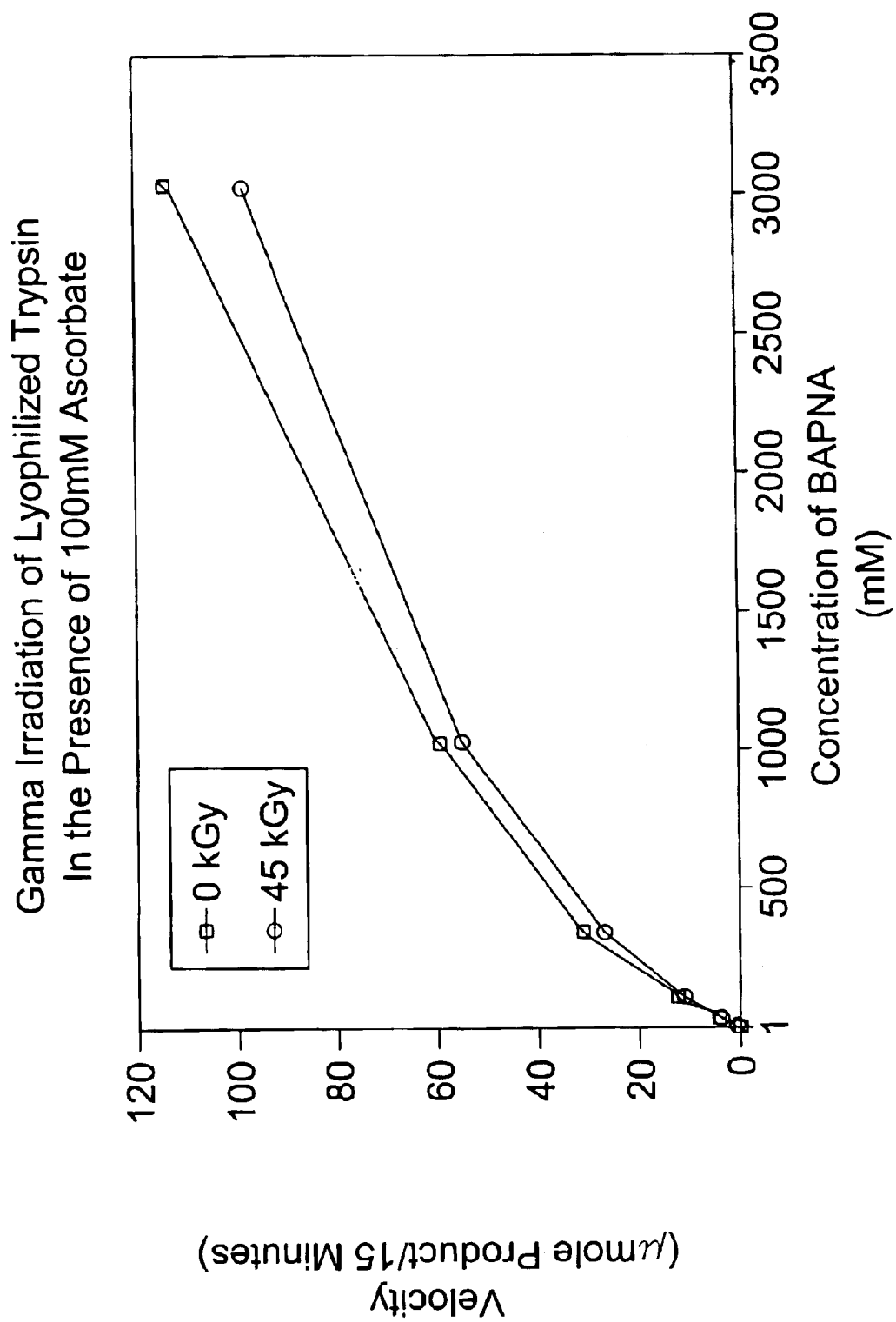

All samples were resuspended in 1 ml water, and then diluted 1:10 for assay. Assay conditions: 50 units/ml trypsin per well+BAPNA substrate starting at 3000 $\mu$g/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).
Results In the absence of stabilizer, trypsin (3.9% water) exposed to 45 kGy total dose gamma-irradiation showed recovery of 77% of control activity. In the presence of stabilizer, trypsin (0.7% water) exposed to 45 kGy total dose gamma-irradiation showed recovery of 86% of control activity. The results of this experiment are shown graphically in FIGS. 4A–4B.

Example 5

In this experiment, lyophilized trypsin was irradiated (45 kGy at 1.9 kGy/hr) alone or in the presence of a stabilizer (sodium ascorbate 100 mM) at varying levels of residual solvent content.
Method 1 ml aliquots of trypsin alone or with 100 mM sodium ascorbate (10 mg/ml) were placed in 3 ml vials. Samples were prepared in triplicate and subjected to lyophilization, either a primary drying cycle (25 hours, sample temp 0–10° C., shelf temp 35° C., 10 mT) or a combination of a primary drying cycle and a secondary drying cycle (65 hours, sample temp 40° C., shelf temp 40° C., 10 mT).

All samples were resuspended in 1 ml water, and then diluted 1:10 for assay. Assay conditions: 50 units/ml trypsin per well+BAPNA substrate starting at 3000 pg/ml was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).
Results In the absence of stabilizer, trypsin exposed to 45 kGy total dose gamma-irradiation showed recovery of 74% of control activity at the higher residual solvent content level, i.e. about 5.8% water, and recovery of 77% of control activity at the lower residual solvent content level, i.e., about 5.4% water.

In the presence of stabilizer, trypsin exposed to 45 kGy total dose gamma-irradiation showed recovery of 97% of control activity at higher residual solvent content levels, i.e. about 2.8% water, and recovery of 90% of control activity at lower residual solvent content levels, i.e. about 1.1% water.

Figure 5A:
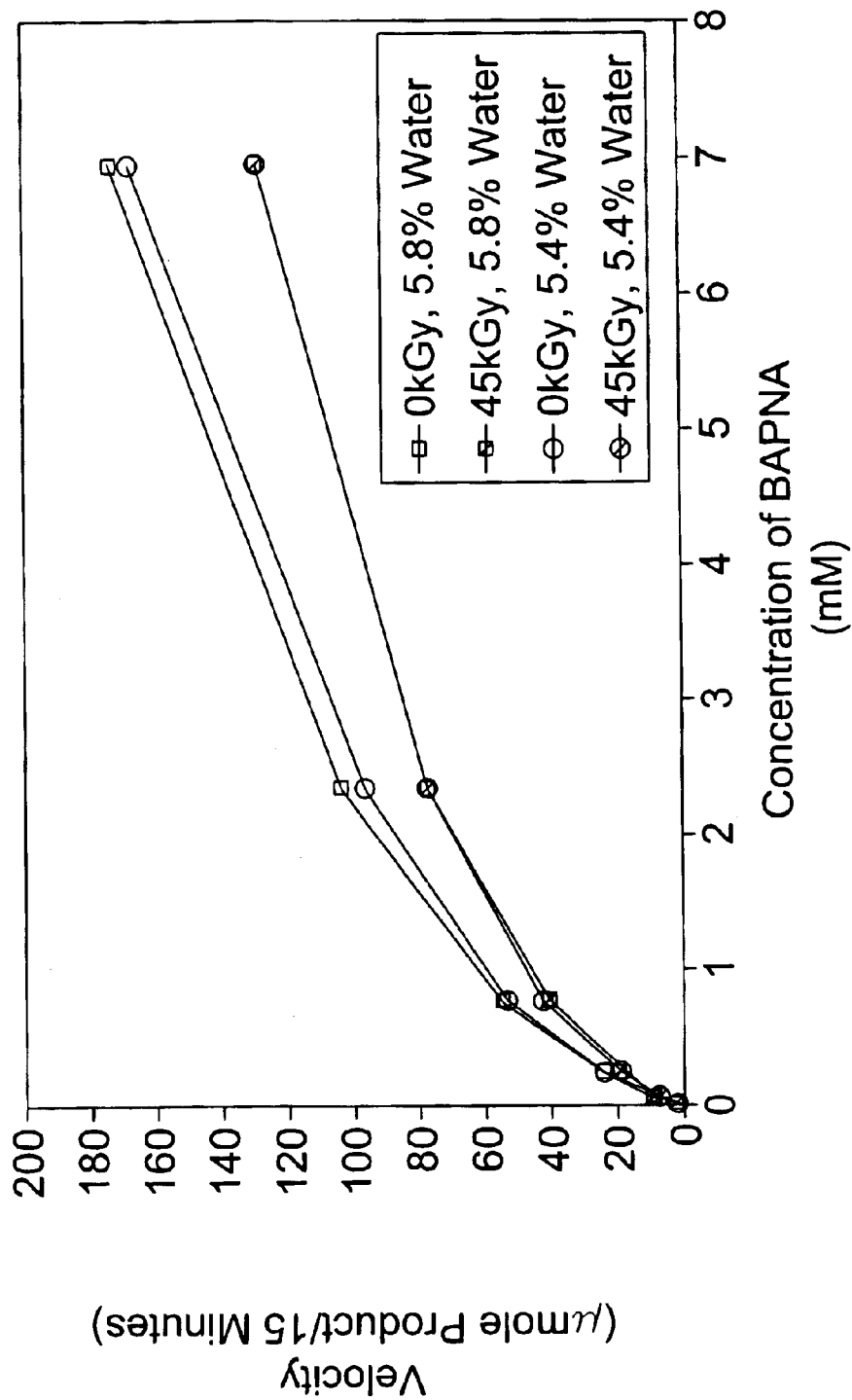
FIGS. 5A–5B are graphs showing the activity of lyophilized trypsin following gamma irradiation in the absence or presence of a stabilizer and at varying levels of residual solvent content.
Figure 5B:
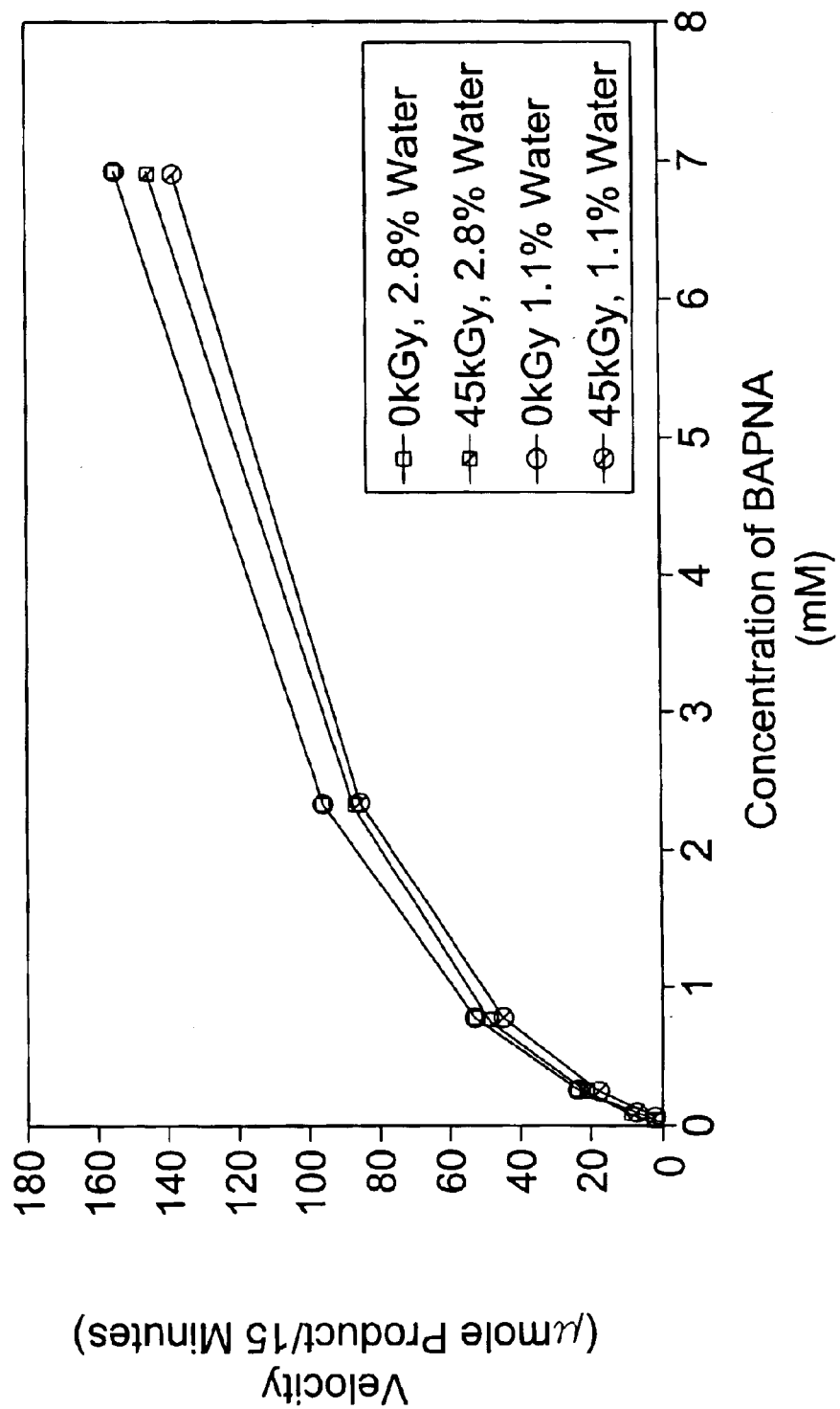

The results of this experiment are shown graphically in FIGS. 5A–5B.

Example 6

In this experiment, trypsin suspended in polypropylene glycol 400 was subjected to gamma irradiation at varying levels of residual solvent (water) content.
Method Trypsin was suspended in polypropylene glycol 400 at a concentration of about 20,000 U/ml and divided into multiple samples. A fixed amount of water (0%, 1%, 2.4%, 4.8%, 7%, 9%, 10%, 20%, 33%) was added to each sample; a 100% water sample was also prepared which contained no PPG 400.

Samples were irradiated to a total dose of 45 kGy at a rate of 1.9 kGy/hr and a temperature of 4° C. Following irradiation, each sample was centrifuged to pellet the undissolved trypsin. The PPG/water soluble fraction was removed and the pellets resuspended in water alone.

Figure 6:
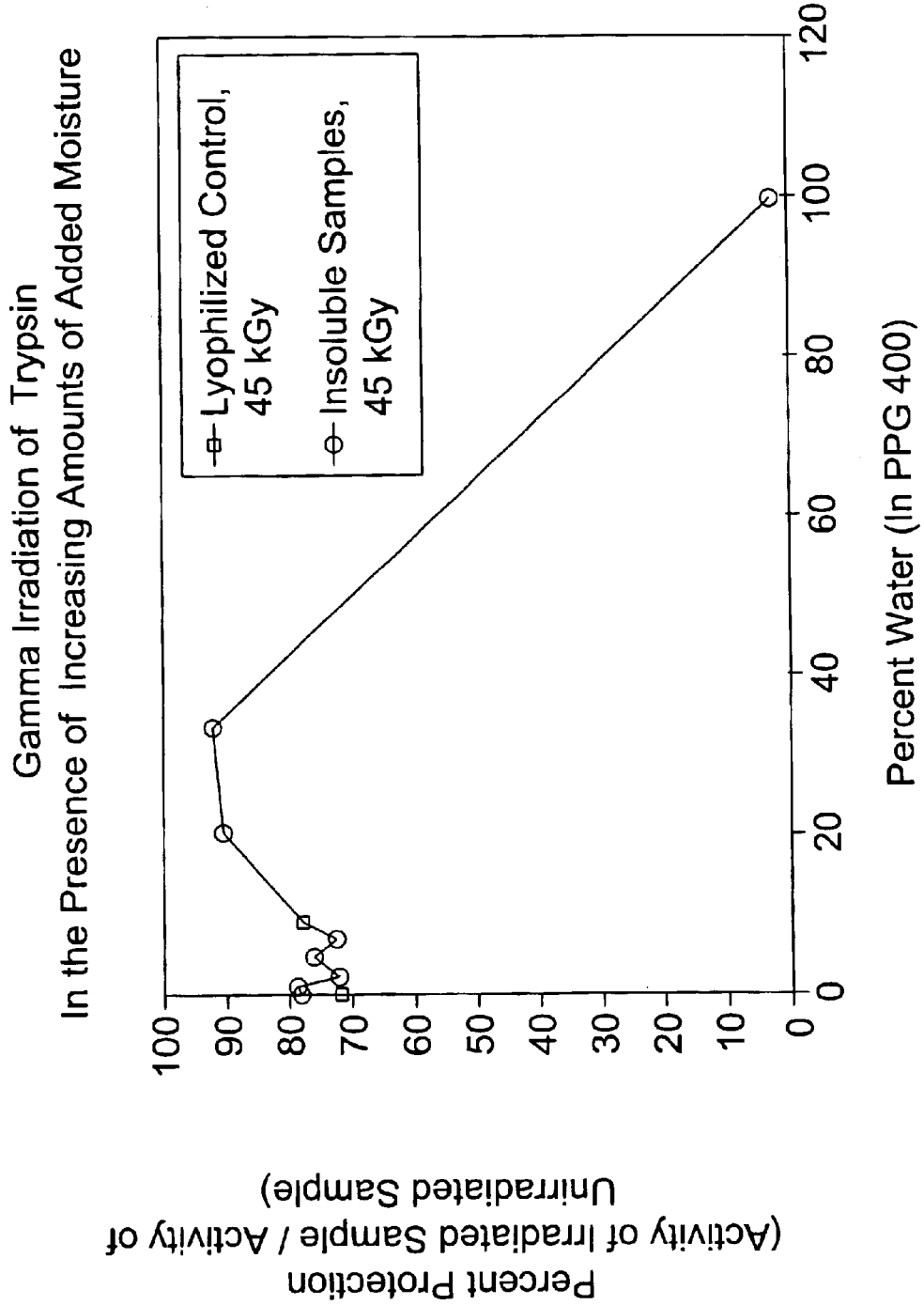
FIG. 6 is a graph showing the activity of trypsin suspended in polypropylene glycol following gamma irradiation at varying levels of residual solvent content.

Assay conditions: 5 U/well trypsin (50 U/ml)+BAPNA substrate (0.5 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 mn to obtain a corrected absorption value. The change in this value over time between 5 and 15 minutes of reaction time was plotted and Vmax and Km determined in Sigma Plot using the hyperbolic rectangular equation).
Results The irradiated samples containing a mixture of polypropylene glycol (PPG 400) and water (up to 33% water) retained about 80% of the activity of an unirradiated trypsin control and activity equal to that of a dry (lyophilized) trypsin control irradiated under identical conditions. No activity was detected in the 100% water sample irradiated to 45 kGy. The results of this experiment are shown graphically in FIG. 6.

Example 7

In this experiment, an aqueous solution of trypsin was subjected to gamma irradiation at varying concentrations of a stabilizer (sodium ascorbate, alone or in combination with 1.5 mM uric acid).
Method Trypsin samples (5 Units/sample) were prepared with varying concentrations of sodium ascorbate, alone or in combination with 1.5 mM uric acid. Samples were irradiated to a total dose of 45 kGy at a rate of 1.9 kGy/hr and a temperature of 4° C.

Assay conditions: 5 U/well trypsin (50 U/ml)+50 µl BAPNA substrate (1 mg/ml). The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

Figure 7:
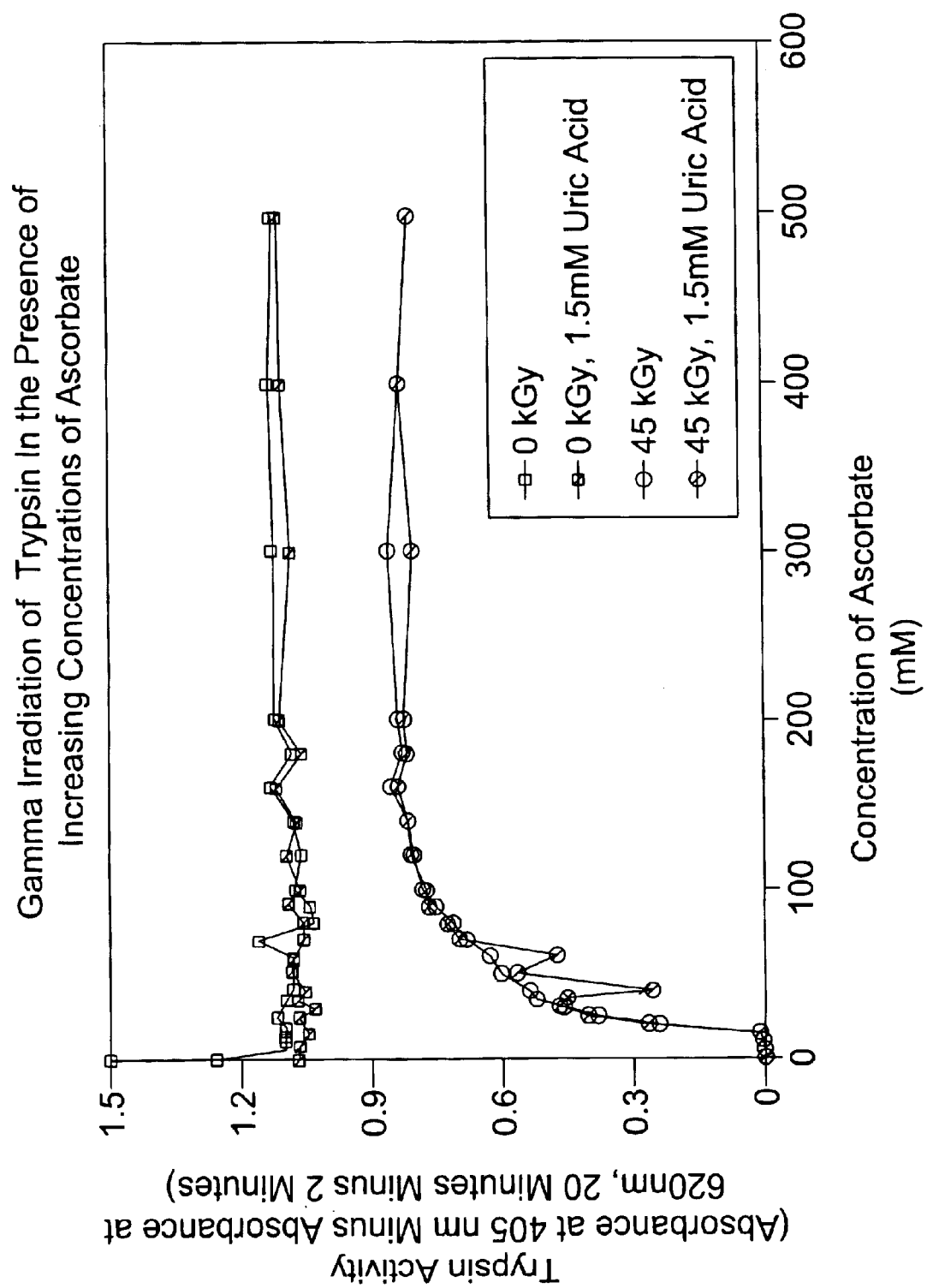
FIG. 7 is a graph showing the activity of trypsin following gamma irradiation in an aqueous solution at varying concentrations of stabilizers.

The irradiated samples containing at least 2 mM ascorbate retained varying levels of trypsin activity compared to an unirradiated control. Samples containing 125 mM or more ascorbate retained about 75% of the trypsin activity of an unirradiated control. Similar results were observed with samples containing ascorbate in combination with uric acid. The results of this experiment are shown graphically in FIG. 7.

Example 8

In this experiment, the protective effect of ascorbate (200 mM) and a combination of ascorbate (200 mM) and Gly-Gly (200 mM) on two different frozen enzyme preparations (a glycosidase and a sulfatase) was evaluated.

Method

In glass vials, 300 µl total volume containing 300 µg of enzyme (1 mg/ml) were prepared with either no stabilizer or the stabilizer of interest. Samples were irradiated with gamma radiation (45 kGy total dose, dose rate and temperature of 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4X-Tris (pH 8.8); 3.3 ml water; 100 µl 10% APS solution; and 10µl TEMED. This solution was then placed in an electrophoresis unit with 1×Running Buffer (15.1 g Tris base; 72.0 g glycine; 5.0 g SDS in 11 water, diluted 5-fold). Irradiated and control samples (1 mg/ml) were diluted with Sample Buffer (+/− beta-ME) in Eppindorf tubes and then centrifuged for several minutes. 20µl of each diluted sample (~10 µg) were assayed.

Results

Figure 8A:
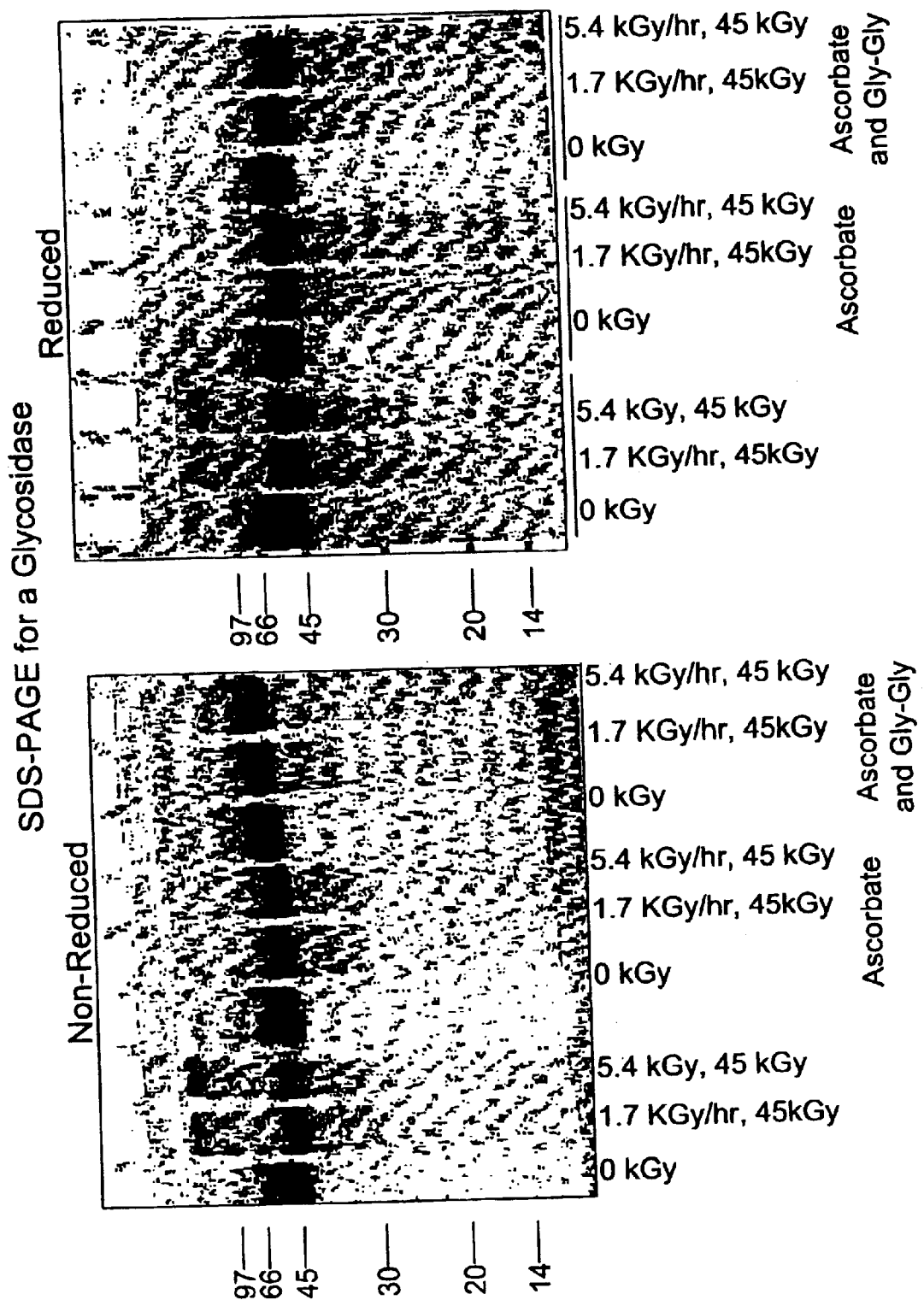
FIGS. 8A–8B are gels showing the protective effect of ascorbate (200 mM) and a combination of ascorbate (200 mM) and Gly-Gly (200 mM) on two different frozen enzyme preparations (a glycosidase and a sulfatase).
Figure 8B:
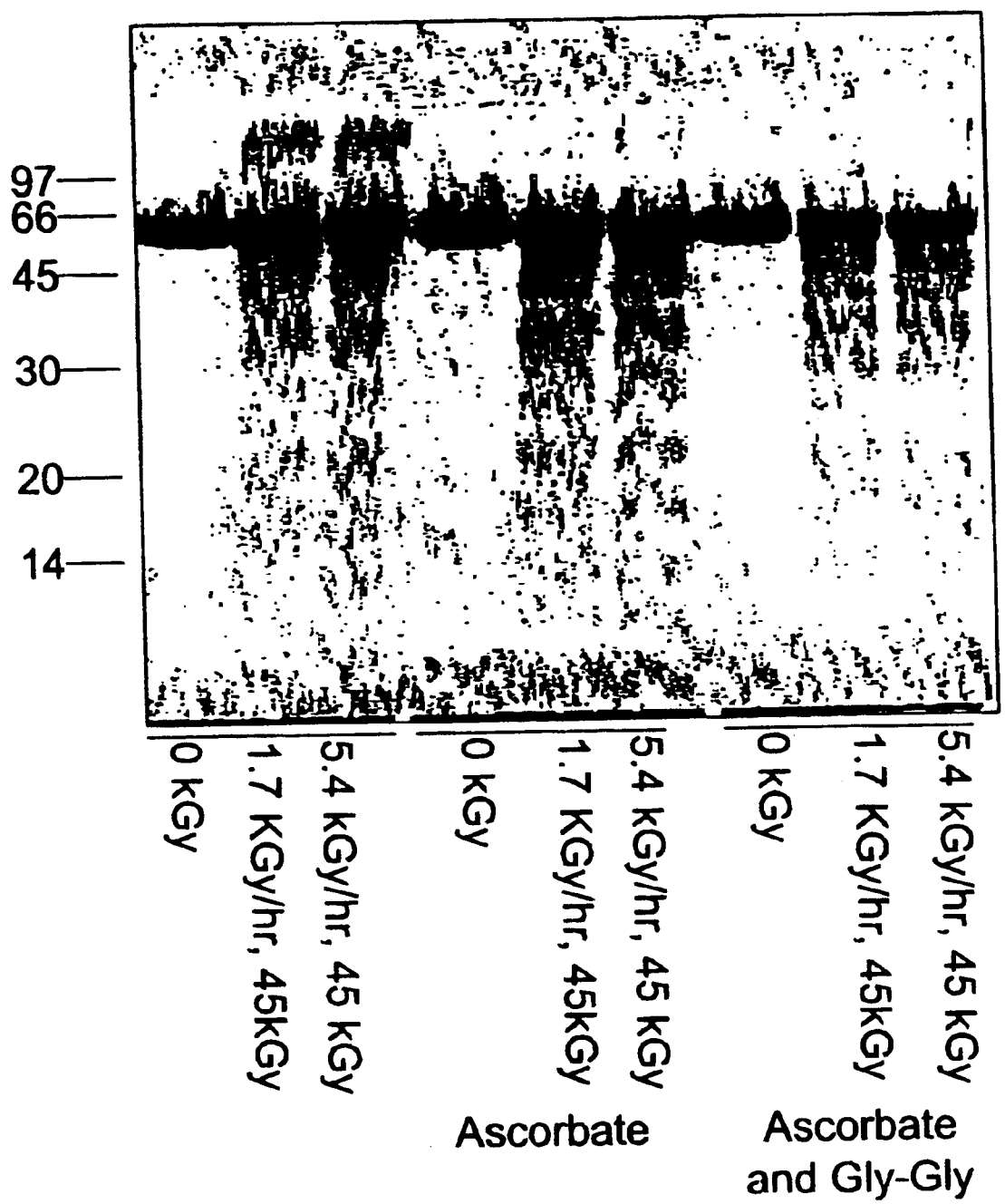

Liquid enzyme samples irradiated to 45 kGy in the absence of a stabilizer showed significant loss of material and evidence of both aggregation and fragmentation. Much greater recovery of material was obtained from the irradiated samples containing ascorbate or a combination of ascorbate and Gly-Gly. The results of this experiment are shown in FIGS. 8A–8B.

Example 9

In this experiment, the protective effect of ascorbate (200 mM) and a combination of ascorbate (200 mM) and Gly-Gly (200 mM) on a frozen glycosidase preparation was evaluated.

Method

Samples were prepared in 2 ml glass vials, each containing 52.6 µl of a glycosidase solution (5.7 mg/ml), and either no stabilizer or a stabilizer of interest, and sufficient water to make a total sample volume of 300 µl. Samples were irradiated with gamma radiation (45 kGy total dose, dose rate and temperature of either 1.616 kGy/hr and −21.5° C. or 5.35 kGy/hr and −21.9° C.) and then assayed for structural integrity.

Structural integrity was determined by reverse phase chromatography. 10 µl of sample were diluted with 90 µl solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Figure 9:
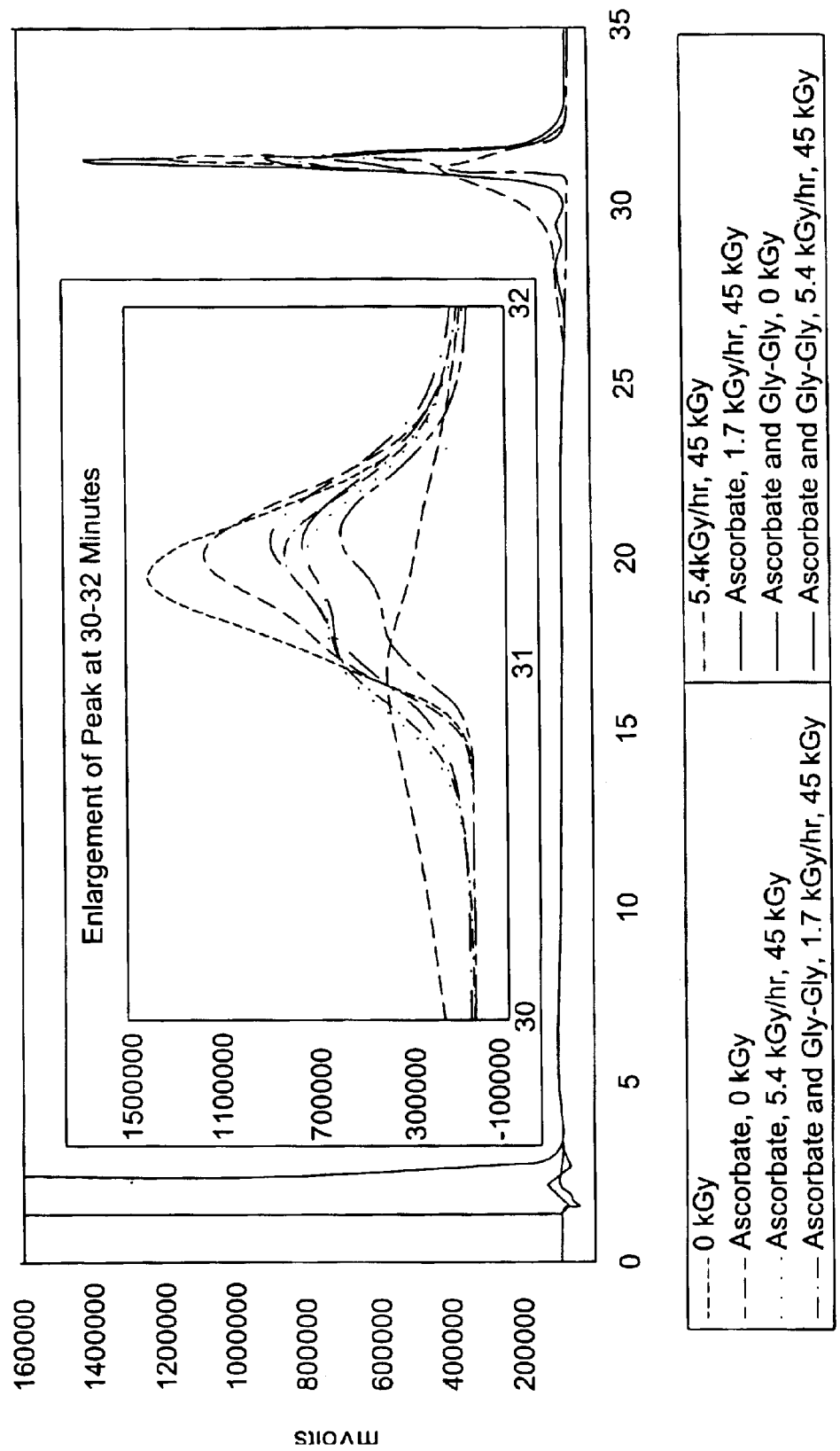
FIG. 9 is a graph showing the protective effect of stabilizers on a frozen glycosidase preparation.

Enzyme samples irradiated to 45 kGy in the absence of a stabilizer showed broadened and reduced peaks. Much greater recovery of material, as evidenced by significantly less reduction in peak size compared to control (FIG. 9), was obtained from the irradiated samples containing ascorbate or a combination of ascorbate and Gly-Gly.

Example 10

In this experiment, lyophilized trypsin was irradiated (45 kGy total dose at 1.9 kGy/hr. at 4° C.) in the presence of Tris buffer (pH 7.6) or phosphate buffer (pH 7.5).

Method

Aliquots of a 1000 IU/ml trypsin solution were placed in 3 ml vials and then lyophilized and gamma-irradiated. The remaining portion of each solution was gamma-irradiated as a liquid. Samples were assayed under the following conditions: Assay conditions: 5 U/well trypsin (50 U/ml)+BATNA substrate (1 mg/ml) was serially diluted 3-fold down a 96-well plate. The assay was set up in two 96-well plates and absorption read at both 405 and 620 nm at 5 and 20 minutes. The absorption at 630 nm (background) was subtracted from the value at 405 nm to obtain a corrected absorption value. The change in this value over time between 5 and 15 minutes of reaction time was plotted and Vmax and Km determined in Sigma Plot using the hyperbolic rectangular equation).

Results

Lyophilized trypsin samples exposed to 45 kGy total dose gamma-irradiation showed recovery of essentially all trypsin activity in the presence of Tris buffer and sodium ascorbate and recovery of 88% of trypsin activity in the presence of phosphate buffer and sodium ascorbate.

Example 11

In this experiment, lyophilized enzyme preparations (a glycosidase and a sulfatase) were irradiated in the absence or presence of a stabilizer (100 mM sodium ascorbate).

Method

Glass vials containing 1 mg of enzyme were prepared with either no stabilizer or 100 mM sodium ascorbate (50lµl of 2M solution) and sufficient water to make 1 ml of sample. Samples were lyophilized following moisture levels: glycosidase with stabilizer, 3.4%; glycosidase without stabilizer, 3.2%; sulfate with stabilizer, 1.8%; and sulfate without stabilizer, 0.7%. Lyophilized samples were irradiated with gamma radiation (45 kGy total dose at 1.8 kGy/hr and 4° C.) and then assayed for structural integrity.

Structural integrity was determined by SDS-PAGE. In an electrophoresis unit, 6 µg/lane of each sample was run at 120V on a 7.5%–15% acrylamide gradient gel with a 4.5% acrylamide stacker under non-reducing conditions.

Results

Lyophilized glycosidase samples irradiated to 45 kGy in the absence of a stabilizer showed significant recovery of intact enzyme with only some fragmentation. Fragmentation was reduced by the addition of a stabilizer.

Similarly, lyophilized sulfatase samples irradiated to 45 kGy in the absence of a stabilizer showed good recovery of intact enzyme, but with slightly more fragmentation. Fragmentation was again reduced by the addition of a stabilizer.

Figure 10:
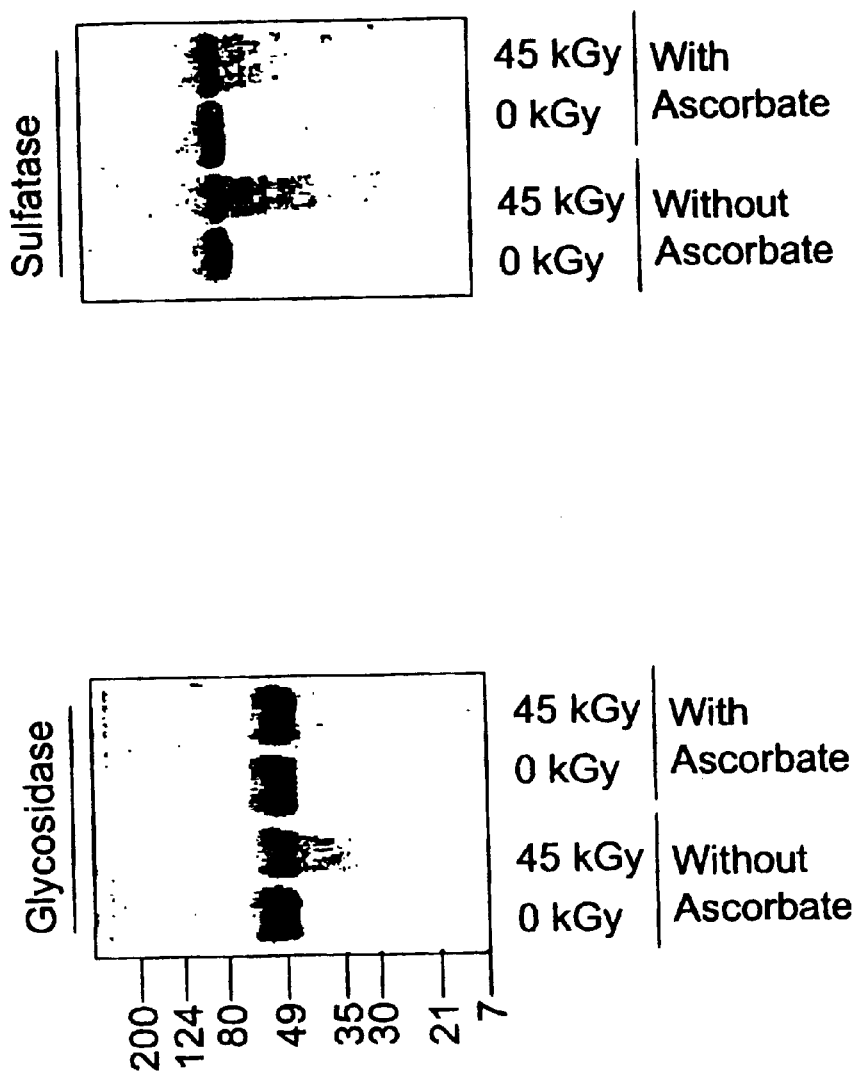
FIG. 10 shows the protective effect of ascorbate on two different lyophilized enzyme preparations (a glycosidase and a sulfatase).

The results of this experiment are shown in FIG. 10.

Example 12

In this experiment, lyophilized glycosidase preparations irradiated in the absence or presence of a stabilizer (200 mM sodium ascorbate or a combination of 200 mM ascorbate and 200 mM glycylglycine).

Methods

Samples were prepared in glass vials, each containing 300 µg of a lyophilized glycosidase and either no stabilizer or a stabilizer of interest. Samples were irradiated with gamma radiation to varying total doses (10 kGy, 30 kGy and 50 kGy total dose, at a rate of 0.6 kGy/hr. and a temperature of −60° C.) and then assayed for structural integrity using SDS-PAGE.

Samples were reconstituted with water to a concentration of 1 mg/ml, diluted 1:1 with 2×sample buffer (15.0 ml 4×Upper Tris-SDS buffer (pH 6.8); 1.2 g sodium dodecyl sulfate; 6 ml glycerol; sufficient water to make up 30 ml; either with or without 0.46 g dithiothreitol), and then heated at 80° C. for 10 minutes. 10 µl of each sample (containing 5 µg of enzyme) were loaded into each lane of a 10% polyacrylamide gel and run on an electrophoresis unit at 125V for about 1.5 hours.

Results

Figure 11A:
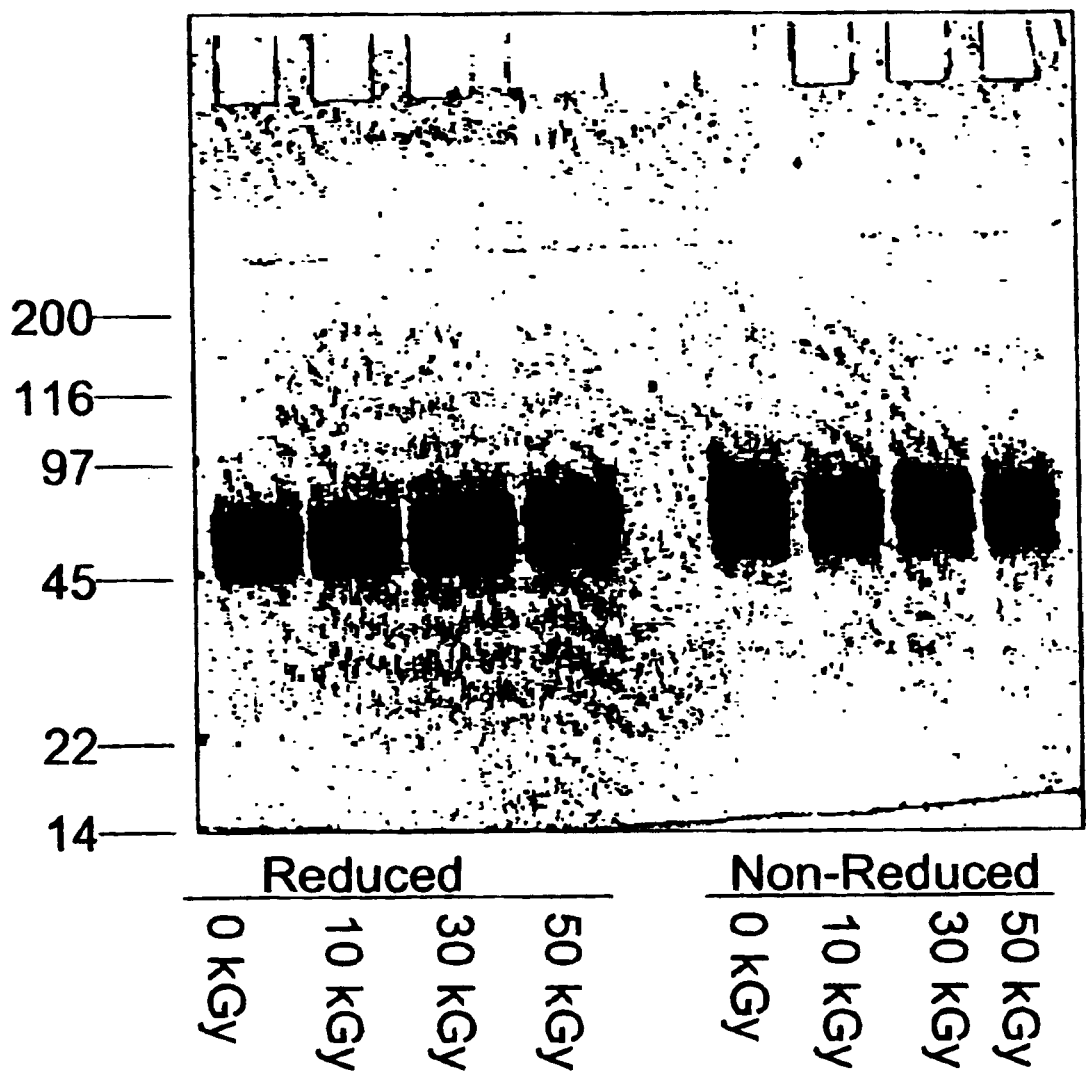
Figure 11B:
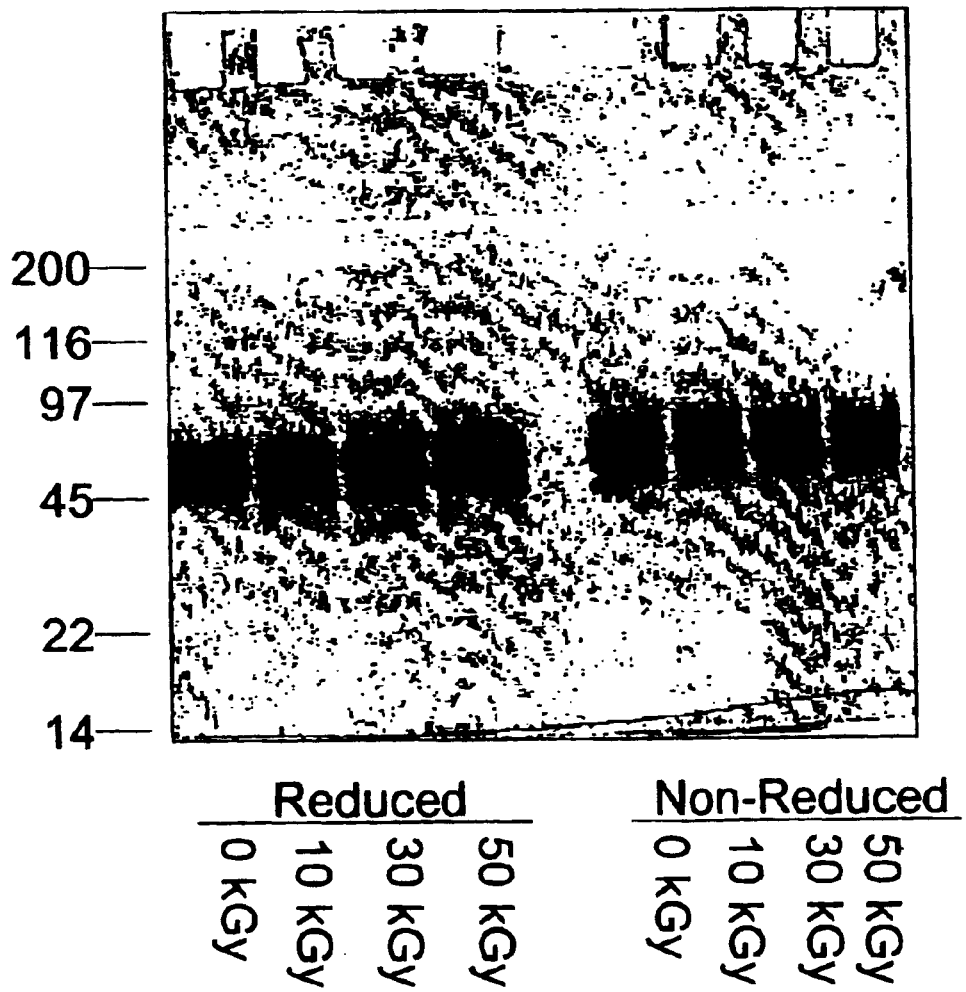
Figure 11C:
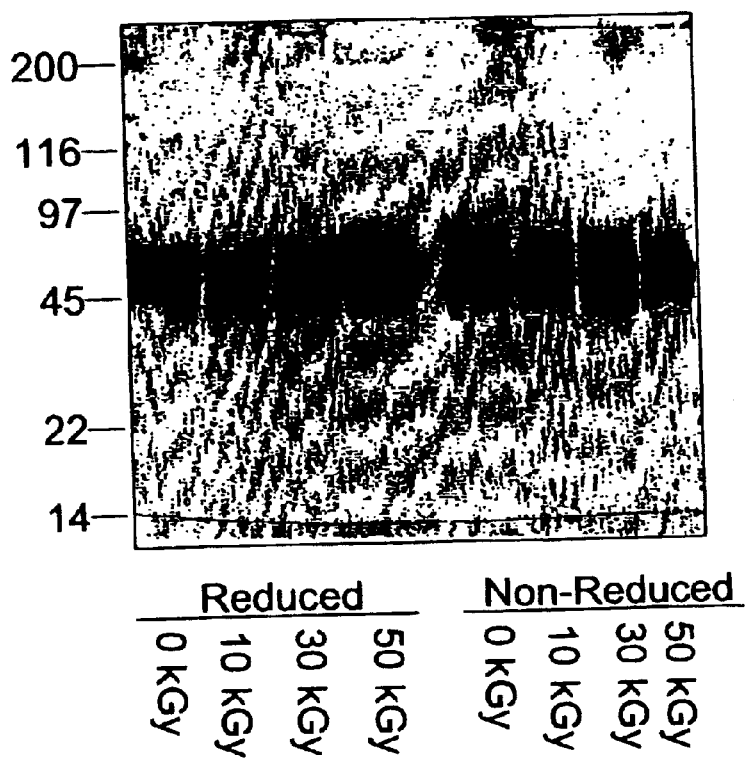

About 80% of the enzyme was recovered following irradiation of the samples containing no stabilizer, with some degradation as shown in FIGS. 11A–11C. Less degradation was observed in the samples containing ascorbate alone as the stabilizer, and even less degradation in the samples containing a combination of ascorbate and glycylglycine as the stabilizer.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for sterilizing a preparation of one or more digestive enzymes that is sensitive to radiation, said method comprising:
   (i) applying to said preparation of one or more digestive enzymes prior to irradiating a stabilizing process of reducing the temperature of said preparation of one or more digestive enzymes below ambient temperature; and
   (ii) irradiating said preparation of one or more digestive enzymes with a suitable radiation at an effective rate for a time effective to sterilize said preparation of one or more digestive enzymes, wherein said stabilizing process and the rate of irradiation are together effective to protect said preparation of one or more digestive enzymes from said radiation.

2. The method according to claim 1, further comprising applying to said preparation of one or more digestive enzymes prior to irradiating at least one additional stabilizing process selected from the group consisting of: (a) reducing the residual solvent content of said preparation of one or more digestive enzymes: and (b) adding at least one stabilizer to said preparation of one or more digestive enzymes, wherein said stabilizing processes are together effective to protect said preparation of one or more digestive enzymes from said radiation and further wherein said stabilizing processes may be performed in any order.

3. The method according to claim 1 or 2, further comprising reducing the residual solvent content of said preparation of one or more digestive enzymes prior to irradiating, wherein said solvent is water.

4. The method according to claim 3, wherein said residual water content is reduced by the addition of an organic solvent.

5. The method according to claim 1 or 2, further comprising reducing the residual solvent content of said preparation of one or more digestive enzymes prior to irradiating, wherein said solvent is an organic solvent.

6. The method according to claim 1 or 2, wherein said preparation of one or more digestive enzymes is suspended in an organic solvent following reduction of a residual solvent content.

7. The method according to claim 1 or 2, wherein said effective rate is not more than 3.0 kGy/hour.

8. The method according to claim 1 or 2, wherein said effective rate is not more than 2.0 kGy/hr.

9. The method according to claim 1 or 2, wherein said effective rate is not more than 1.0 kGy/hr.

10. The method according to claim 1 or 2, wherein said effective rate is not more than 0.3 kGy/hr.

11. The method according to claim 1 or 2, wherein said effective rate is more than 3.0 kGy/hour.

12. The method according to claim 1 or 2, wherein said effective rate is at least 6.0 kGy/hour.

13. The method according to claim 1 or 2, wherein said effective rate is at least 18.0 kGy/hour.

14. The method according to claim 1 or 2, wherein said effective rate is at least 30.0 kGy/hour.

15. The method according to claim 1 or 2, wherein said effective rate is at least 45 kGy/hour.

16. The method according to claim 1 or 2, wherein said preparation of one or more digestive enzymes is maintained in a low oxygen atmosphere.

17. The method according to claim 1 or 2, wherein said preparation of one or more digestive enzymes is maintained in an atmosphere comprising at least one noble gas.

18. The method according to claim 17, wherein said noble gas is argon.

19. The method according to claim 1 or 2, wherein said preparation of one or more digestive enzymes is maintained in a vacuum.

20. The method according to claim 1 or 2, further comprising reducing the residual solvent content of said preparation of one or more digestive enzymes prior to irradiating, wherein said residual solvent content is reduced by a method selected from the group consisting of lyophilization, drying, concentration, addition of solute, evaporation, chemical extraction, spray-drying, vitrification and combinations of two or more thereof.

21. The method according to claim 1 or 2, further comprising reducing the residual solvent content of said preparation of one or more digestive enzymes prior to irradiating, wherein said residual solvent content is less than 15%.

22. The method according to claim 1 or 2, further comprising reducing the residual solvent content of said preparation of one or more digestive enzymes prior to irradiating, wherein said residual solvent content is less than 10%.

23. The method according to claim 1 or 2, further comprising reducing the residual solvent content of said preparation of one or more digestive enzymes prior to irradiating, wherein said residual solvent content is less than 3%.

24. The method according to claim 1 or 2, further comprising reducing the residual solvent content of said preparation of one or more digestive enzymes prior to irradiating wherein said residual solvent content is less than 2%.

25. The method according to claim 1 or 2, further comprising reducing the residual solvent content of said preparation of one or more digestive enzymes prior to irradiating, wherein said residual solvent content is less than 1%.

26. The method according to claim 1 or 2, further comprising reducing the residual solvent content of said preparation of one or more digestive enzymes prior to irradiating, wherein said residual solvent content is less than 0.5%.

27. The method according to claim 1 or 2, further comprising reducing the residual solvent content of said preparation of one or more digestive enzymes prior to irradiating wherein said residual solvent content is less than about 0.08%.

28. The method according to claim 1 or 2, wherein at least one sensitizer is added to said preparation of one or more digestive enzymes prior to said step of irradiating said preparation of one or more digestive enzymes.

29. The method according to claim 1 or 2, wherein said preparation of one or more digestive enzymes contains at least one biological contaminant or pathogen selected from the group consisting of viruses, bacteria, yeasts, molds, fungi, prions or similar agents responsible, alone or in combination, for TSEs and single or multicellular parasites.

30. The method according to claim 1 or 2, further comprising adding an effective amount of at least one stabilizer to said preparation of one or more digestive enzymes prior to irradiating, wherein said at least one stabilizer comprises an antioxidant.

31. The method according to claim 1 or 2, further comprising adding an effective amount of least one stabilizer to said preparation of one or more digestive enzymes prior to irradiating, wherein said at least one stabilizer comprises a free radical scavenger.

32. The method according to claim 1 or 2, further comprising adding an effective amount of least one stabilizer to said preparation of one or more digestive enzymes prior to irradiating, wherein said at least one stabilizer is a combination stabilizer.

33. The method according to claim 1 or 2, further comprising adding an effective amount of least one stabilizer to said preparation of one or more digestive enzymes prior to irradiating, wherein said at least one stabilizer comprises a ligand.

34. The method according to claim 33, wherein said ligand is heparin.

35. The method according to claim 1 or 2, further comprising adding an effective amount of least one stabilizer to said preparation of one or more digestive enzymes prior to irradiating, wherein said at least one stabilizer reduces damage due to reactive oxygen species.

36. The method according to claim 1 or 2, further comprising adding an effective amount of least one stabilizer to said preparation of one or more digestive enzymes prior to irradiating, wherein said at least one stabilizer is selected from the group consisting of: ascorbic acid or a salt or ester thereof, glutathione; 6-hydroxy-2,5,7,8-tetramethylchroman-2-carboxylic acid; uric acid or a salt or ester thereof; methionine; histidine; N-acetyl cysteine; lipoic acid; sodium formaldehyde sulfoxylate; gallic acid or a derivative thereof; propyl gallate and mixtures of two or more thereof.

37. The method according to claim 36, wherein said mixtures of two or more additional stabilizers are selected from the group consisting of: mixtures of ascorbic acid, or a salt or ester thereof, and uric acid, or a salt or ester thereof; mixtures of ascorbic acid, or a salt or ester thereof, and 6-hydroxy-2,5,7,8-tetramethylchroman-2-carboxylic acid, mixtures of ascorbic acid, or a salt or ester thereof, uric acid, or a salt or ester thereof, and 6-hydroxy-2,5,7,8-tetramethylchroman-2-carboxylic acid; and mixtures of uric acid, or a salt or ester thereof, lipoic acid, sodium formaldehyde sulfoxylate, gallic acid or a derivative thereof, propyl gallate and 6-hydroxy-2,5,7,8-tetramethylchroman-2-carboxylic acid.

38. The method according to claim 1 or 2, further comprising adding an effective amount of least one stabilizer to said preparation of one or more digestive enzymes prior to irradiating, wherein said at least one stabilizer is a dipeptide stabilizer.

39. The method according to claim 38, wherein said dipeptide stabilizer is selected from the group consisting of glycyl-glycine (Gly-Gly), carnosine, anserine and combinations of two or more thereof.

40. The method according to claim 1 or 2, wherein said radiation is corpuscular radiation or electromagnetic radiation, or a mixture thereof.

41. The method according to claim 40, wherein said electromagnetic radiation is selected from the group consisting of radio waves, microwaves, visible and invisible light, ultraviolet light, x-ray radiation, gamma radiation and combinations thereof.

42. The method according to claims 1 or 2, wherein said radiation is gamma radiation.

43. The method according to claim 1 or 2, wherein said radiation is E-beam radiation.

44. The method according to claim 1 or 2, wherein said radiation is visible light.

45. The method according to claim 1 or 2, wherein said radiation is ultraviolet light.

46. The method according to claim 1 or 2, wherein said radiation is x-ray radiation.

47. The method according to claim 1 or 2, wherein said radiation is polychromatic visible light.

48. The method according to claim 1 or 2, wherein said radiation is infrared.

49. The method according to claim 1 or 2, wherein said radiation is a combination of one or more wavelengths of visible and ultraviolet light.

50. The method according to claim 1 or 2, wherein said irradiation is conducted at a temperature below ambient temperature.

51. The method according to claim 1 or 2, wherein said irradiation is conducted below the freezing point of said preparation of one or more digestive enzymes.

52. The method according to claim 1 or 2, wherein said irradiation is conducted below the eutectic point of said preparation of one or more digestive enzymes.

53. The method according to claim 1 or 2, further comprising adding an effective amount of at least one stabilizer to said preparation of one or more digestive enzymes prior to irradiating.

* * * * *